(12) United States Patent
Josephson et al.

(10) Patent No.: US 12,369,964 B2
(45) Date of Patent: *Jul. 29, 2025

(54) SKIN TAG REMOVAL DEVICES

(71) Applicant: DGI Group LLC, Howell, NJ (US)

(72) Inventors: Jeremy Josephson, Lakewood, NJ (US); Zachary Lind, Lakewood, NJ (US)

(73) Assignee: DGI Group LLC, Howell, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,045

(22) Filed: May 22, 2023

(65) Prior Publication Data

US 2024/0099755 A1 Mar. 28, 2024

Related U.S. Application Data

(62) Division of application No. 17/951,361, filed on Sep. 23, 2022.

(51) Int. Cl.
*A61B 18/02* (2006.01)
*A61B 17/00* (2006.01)
*A61B 18/00* (2006.01)

(52) U.S. Cl.
CPC .. *A61B 18/0218* (2013.01); *A61B 2017/0023* (2013.01); *A61B 2018/00095* (2013.01); *A61B 2018/00101* (2013.01); *A61B 2018/0047* (2013.01); *A61B 2018/0225* (2013.01)

(58) Field of Classification Search
None
See application file for complete search history.

(56) References Cited

U.S. PATENT DOCUMENTS

| 9,402,675 | B2 | 8/2016 | Lind |
| 2002/0173780 | A1 | 11/2002 | Altshuler et al. |
| 2004/0102768 | A1* | 5/2004 | Cluzeau ............ A61B 18/0218 606/26 |

(Continued)

OTHER PUBLICATIONS

United States Patent and Trademark Office Action in U.S. Appl. No. 18/200,044, filed Apr. 24, 2024.

(Continued)

*Primary Examiner* — Linda C Dvorak
*Assistant Examiner* — Nora W Rhodes
(74) *Attorney, Agent, or Firm* — Weiss & Arons LLP

(57) ABSTRACT

A tip for application of cryogenic matter onto a skin lesion includes a conduit configured to receive therein cryogenic matter; an absorbent application element configured to absorb and contain the cryogenic matter from the conduit and having an exposed face configured to apply the cryogenic matter directly onto the skin lesion; a thermally conductive material arranged in contact with at least a portion of the absorbent application element, said thermally conductive material configured to conduct cold from the absorbent application element and comprising a lip extending circumferentially at least partially around a perimeter of the exposed face; and a layer of insulating material disposed exterior to portions of the thermally conductive material. A device for application of cryogenic matter onto a skin lesion includes an applicator body with two opposing tweezer arms and at least one canister containing cryogenic matter; and first and second disposable tips.

25 Claims, 22 Drawing Sheets

(56) References Cited

U.S. PATENT DOCUMENTS

| | | | |
|---|---|---|---|
| 2008/0132826 A1* | 6/2008 | Shadduck | A61B 18/04 |
| | | | 604/114 |
| 2011/0040361 A1* | 2/2011 | Levy | A61F 7/10 |
| | | | 607/114 |
| 2012/0089211 A1 | 4/2012 | Curtis et al. | |
| 2012/0095395 A1* | 4/2012 | Haery | A61M 25/09 |
| | | | 604/93.01 |
| 2013/0012932 A1* | 1/2013 | Lind | A61B 18/02 |
| | | | 606/23 |
| 2014/0303696 A1* | 10/2014 | Anderson | A61F 7/02 |
| | | | 607/104 |
| 2015/0223975 A1 | 8/2015 | Anderson et al. | |
| 2021/0378727 A1 | 12/2021 | Goulko et al. | |
| 2022/0296265 A1 | 9/2022 | Rutt | |
| 2022/0354567 A1* | 11/2022 | Melman | H04L 63/083 |

OTHER PUBLICATIONS

United States Patent and Trademark Office Action in U.S. Appl. No. 18/200,046, filed Apr. 24, 2024.
United States Patent and Trademark Office Action in U.S. Appl. No. 17/951,361, filed Feb. 20, 2024.
United States Patent and Trademark Office Action in U.S. Appl. No. 17/951,361, filed Jun. 20, 2024.

* cited by examiner

SKIN TAG REMOVAL DEVICES

CROSS-REFERENCE TO RELATED APPLICATIONS

This application is a divisional of U.S. application Ser. No. 17/951,361, filed on Sep. 23, 2022, which is hereby incorporated by reference herein in its entirety.

FIELD OF THE INVENTION

The present disclosure relates to methods and devices for treating skin lesions, and more specifically, but not exclusively, to an improved tip for application of cryogenic matter onto a skin tag, wherein the tip is suitable for integration into a tweezers type device for application of cryogenic matter directly onto the skin tag.

BACKGROUND OF THE INVENTION

Treating skin lesions, such as skin tags or warts, by freezing with cryogenic matter is generally known. Various devices have been developed for freezing of skin lesions using cryogenic matter. For example, a device designed for treatment of warts may include a receptacle for cryogenic matter and an applicator tip. When it is desired to freeze the skin lesion, the cryogenic matter is released to the application tip, thereby cooling the applicator tip, and the applicator tip is applied to the wart. Similar devices designed for application onto skin tags require a shield that is placed around the skin surrounding the skin tag, to prevent the surrounding skin from being damaged.

U.S. Pat. No. 9,402,675, which is assigned to the same assignee as the present application, discloses various embodiments of a tweezers device for application of cryogenic matter directly on a skin tag while protecting the collateral skin tissue from being damaged by the cryogenic matter. Exemplary tweezers devices covered by the '675 patent are commercially available under the trademark Claritag®.

When applying cryogenic matter onto a skin tag, it is particularly desirable to apply the cryogenic matter to the base of the skin tag, i.e., the section of the skin tag that is closest to the junction with a surface of the skin. Applying the cryogenic matter to the base of the skin tag is advantageous, inter alia, to ensure that the entire skin tag is frozen by the cryogenic matter. It is also advantageous to ensure that the cryogenic matter is applied onto the base of the skin tag regardless of the precise orientation of the device applying the cryogenic matter. It is further desirable to provide a user with a visual and/or tactile indication to help determine that the cryogenic matter is indeed being applied to the base of the skin tag.

Existing tweezers devices are designed to be applied to skin lesions with the devices held at particular orientations relative to the skin. These devices may be less reliable when held at different orientations relative to the skin. In addition, when using existing tweezers devices for applying cryogenic matter to a skin tag, it is necessary to at least partially obscure the skin tag with the tweezers device itself. This obscuring further reduces the certainty of the user that he or she has successfully applied cryogenic matter to the entire skin tag.

SUMMARY OF THE INVENTION

It is an object of the present disclosure to provide an improved tip for application of cryogenic matter onto a skin tag, which may provide a high degree of certainty that cryogenic matter is applied to the base of the skin tag. It is another object of the present disclosure to provide an improved tweezers device using the improved tip, for application of cryogenic matter onto a skin tag.

The present disclosure addresses these objectives by providing a tip including a thermally conductive material. The thermally conductive material is arranged in contact with at least a portion of an absorbent application element that absorbs cryogenic matter. The thermally conductive material is configured to be cooled by the absorbent application element. The thermally conductive material includes a lip extending circumferentially at least partially around a perimeter of an exposed face of the absorbent application element. Due to the presence of the lip of thermally conductive material, the tip is particularly well suited to grasp a base portion of a skin tag. Specifically, the lip may be situated at a portion of the tip that typically is situated closest to the surface of the skin. The lip may likewise extend circumferentially around a substantial portion of the perimeter of the tip, to ensure that the lip contacts the base of the skin tag regardless of the specific orientation of the tip relative to the skin tag. Likewise, the lip provides to the user a tactile sensation of the lowest point on the skin tag that is being grasped, thereby affording further assurance of successful treatment of the base of the skin tag.

The tips and tweezers devices described herein are suitable for treatment of skin tags on both humans and on domesticated animals such as dogs.

According to a first aspect, a tip for application of cryogenic matter onto a skin lesion is disclosed. The tip includes a conduit for receiving therein cryogenic matter; an absorbent application element configured to absorb and contain cryogenic matter from the conduit and having an exposed face for applying the cryogenic matter directly onto the skin lesion; a thermally conductive material arranged in contact with at least a portion of the absorbent application element, said thermally conductive material being configured to conduct cold from the absorbent application element and comprising a lip extending at least partially around a perimeter of the exposed face; and a layer of insulating material configured exterior to portions of the thermally conductive material that are not part of the lip.

In another implementation according to the first aspect, the thermally conductive material comprises a casing that is disposed around an entire perimeter of the absorbent application element. The lip may extend around less than the entire perimeter of the casing.

In another implementation according to the first aspect, the lip extends around at least a bottom half of the absorbent application element, said bottom half defined as the half that is closer to skin collateral to the lesion when the conduit is arranged perpendicular to the skin.

In another implementation according to the first aspect, the thermally conductive material includes stainless steel.

In another implementation according to the first aspect, the insulating material includes plastic.

In another implementation according to the first aspect, the absorbent application element comprises open cell foam.

According to a second aspect, a device for application of cryogenic matter directly on a skin lesion while protecting collateral skin tissue from being damaged by the cryogenic matter is disclosed. The device includes: an applicator body having first and second opposing tweezer arms, with a plurality of canisters containing cryogenic matter; and first and second disposable tips, each disposable tip mechanically connected to an end of a respective tweezer arm. Each disposable tip includes: a conduit for receiving therein cryogenic matter; an absorbent application element configured to absorb and contain cryogenic matter and having an exposed face for applying the cryogenic matter directly onto the skin lesion when the first and second opposing tweezer arms are closed; a thermally conductive material arranged in contact with at least a portion of the absorbent application element, said thermally conductive material being configured to conduct cold from the absorbent application element, wherein the thermally conductive material includes a lip extending at least partially around a perimeter of the exposed face; and a layer of insulating material configured exterior to portions of the thermally conductive material that are not part of the lips. When cryogenic matter is delivered from the canisters to the first and second application elements, and the tweezer arms are placed around the skin lesion and are squeezed together, the lips freeze the base of the skin lesion, and the exposed faces of the absorbent application elements freeze a portion of the skin lesion distal to the base (i.e., the distal portion being that portion of the skin lesion disposed further away from the collateral skin than the base of the skin lesion).

In another implementation according to the second aspect, the thermally conductive material comprises a casing disposed around an entire perimeter of the absorbent application element. The lip may extend around less than the entire perimeter of the casing.

In another implementation according to the second aspect, the lip extends around at least a bottom half of the absorbent application element, said bottom half defined as the half that is closer to skin collateral to the lesion when the conduit is arranged perpendicular to the skin.

In another implementation according to the second aspect, the thermally conductive material includes stainless steel.

In another implementation according to the second aspect, the insulating material includes plastic.

In another implementation according to the second aspect, the absorbent application element comprises open cell foam.

In another implementation according to the second aspect, each of said first and second tweezer arms includes a hollow interior region; the plurality of canisters comprise first and second canisters, each respective canister disposed within said hollow interior region of the respective first and second tweezer arms; and further comprising, for each respective tweezer arm, a connector for delivering cryogenic matter from the canister to the disposable tip.

Each canister may further comprise a spring-actuated nozzle for release of cryogenic matter from each respective canister. The spring-actuated nozzle may comprise a spring-like mechanism. The spring-actuated nozzle may comprise a spring.

The device may further include a charging base configured to receive at least the disposable tips therein, wherein downward depression of the applicator body upon and/or within the charging base causes compression of the springs, thereby releasing cryogenic matter from each respective canister and delivering cryogenic matter through each respective connector to each respective conduit.

The charging base may comprise a plurality of receptacles configured to hold the disposable tips, and a plurality of guiding ridges configured to receive at least part of the applicator body therein during attachment of the applicator body to the disposable tips held within the receptacles.

When the applicator body is moved downwardly upon and/or within the charging base, a space may remain between the first and second absorbent application elements, thereby permitting convection of air therebetween.

In another implementation according to the second aspect, the lips are angled downward away from the absorbent application element.

In another implementation according to the second aspect, each disposable tip further comprises at least one cross spar. Cross spars are configured to prevent exit of the skin lesion through a gap between opposing disposable tips. The cross spars are configured to close over each other when the opposing tweezer arms are closed. Alternatively, a cross spar may close over a non-cross spar-bearing side of an opposing disposable tip. Alternatively, a cross spar on a first disposable tip may close above and/or below a cross spar on a second disposable tip.

According to a third aspect, a device for application of cryogenic matter directly on a skin lesion while protecting collateral skin tissue from being damaged by the cryogenic matter is disclosed. The device includes an applicator body having first and second opposing tweezer arms. The device includes a canister containing cryogenic matter; the canister may be a single canister containing cryogenic material. The device includes first and second disposable tips, each disposable tip mechanically connected to an end of a respective tweezer arm. The device includes a Y-shaped feeder for delivery of cryogenic matter from an outlet of the canister to the first and second disposable tips. Each tweezer arm includes an actuation mechanism that, when relaxed, allows the cryogenic matter to remain sealed in the canister, and, when actuated, permits flow of cryogenic matter from the canister to the Y-shaped feeder. The actuation mechanism of a tweezer arm may be situated at least partly internal to the tweezer arm.

In another implementation according to the third aspect, the actuation mechanism includes a valve member positioned between an outlet of the canister and an inlet of the Y-shaped feeder. Actuation of the internal actuation mechanism causes displacement of the valve member, thereby opening a valve and permitting cryogenic matter to flow from the outlet of the canister to the inlet of the Y-shaped feeder. The actuation mechanism of each tweezer arm may further comprise a hand grip on the tweezer arm, each hand grip operatively connected to a lever configured to displace the valve member; the lever may be disposed at least partly internal to the tweezer arm.

Another implementation according to the single-canister third aspect may be configured with a straight-tube feeder rather than a Y-shaped feeder. The straight-tube feeder implementation may be valved, sealed and actuated as described above for the Y-shaped feeder implementation. When actuated, the straight-tube feeder implementation may directly flow cryogenic matter unto and into the compressed-together absorbent application elements of the first and second disposable tips.

According to a fourth aspect, a method for application of cryogenic matter directly on a skin lesion while protecting collateral skin tissue from being damaged by the cryogenic matter is disclosed. The method includes the step of delivering cryogenic matter from one or more than one canister to first and second absorbent application elements of a tweezers device, the device comprising an applicator body having first and second opposing tweezer arms, and first and second disposable tips, each disposable tip mechanically connected to an end of a respective tweezer arm, wherein each disposable tip comprises an absorbent application element configured to absorb and contain cryogenic matter and having an exposed face for application of the cryogenic matter directly on the skin lesion when the first and second opposing tweezer arms are closed; a thermally conductive material arranged around at least a portion of absorbent application element, said thermally conductive material configured to conduct cold from the absorbent application element, wherein the thermally conductive material includes a lip extending at least partially around a perimeter of the exposed face; and a layer of skin-protective insulating material disposed exterior to portions of the thermally conductive material, with at least part of the lips being free of the insulating material. The method further includes the steps of closing the tweezer arms about the skin lesion; and, thereby, freezing a base of the skin lesion with the lips, and freezing a distal portion of the skin lesion with the exposed faces of the absorbent application elements.

In another implementation according to the fourth aspect, the delivering step comprises actuating one or more than one spring-operated nozzle to thereby deliver cryogenic matter from the one or more than one canister to one or more than one conduit. In another implementation according to the fourth aspect, the actuating step comprises depressing the applicator body upon and/or within a charging base to thereby apply upward pressure on the springs with the tips.

DETAILED DESCRIPTION OF THE INVENTION

Figure 1A:
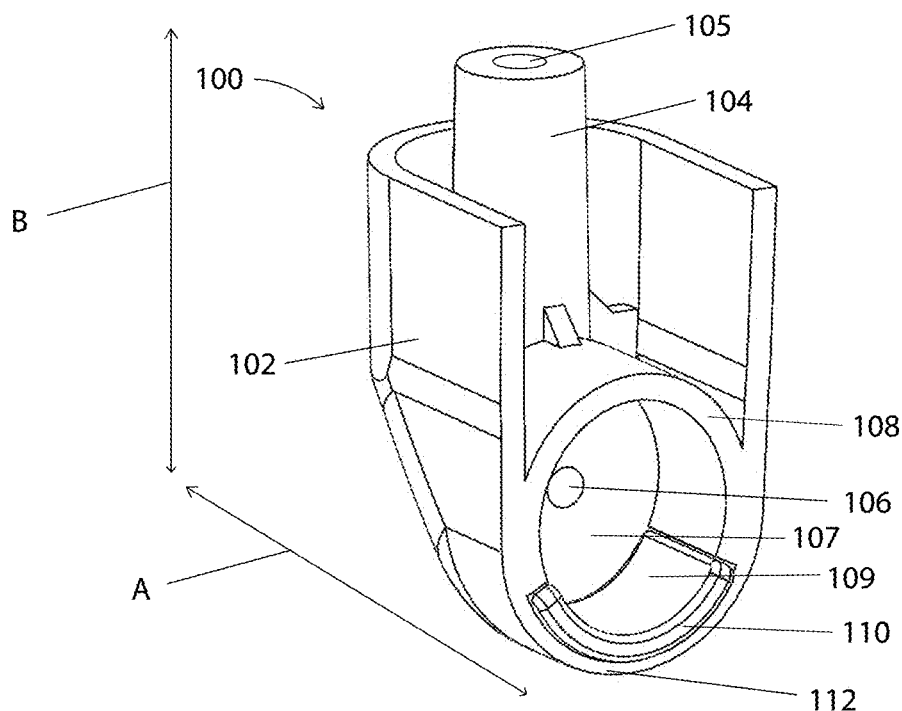
FIGS. 1A and 1B depict an embodiment of a tip for application of cryogenic matter onto a skin lesion, according to embodiments of the present disclosure.

The present disclosure relates to methods and devices for treating skin lesions, and more specifically, but not exclusively, to an improved tip for application of cryogenic matter onto a skin lesion, wherein the tip is suitable for integration into a tweezers type device for application of cryogenic matter directly onto a skin lesion.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

As used in the present disclosure, the term "skin lesion" refers to any part of the skin that has an abnormal growth or appearance compared to the skin around it. Examples of skin lesions include, but are not limited to, warts, cysts, and skin tags. A skin lesion may be on the skin of a human or of any domestic animal, such as a dog. Throughout this disclosure, the devices and methods for treatment of skin lesions are described in reference to skin tags. It should be understood to those of skill in the art that the devices and methods described herein may be applied to cryogenic treatment of any skin lesion, with variation as necessary in order to match the physical shapes of each skin lesion.

As used in the present disclosure, the term "skin tag" refers to a small, benign skin growth that is raised from the skin surface on a fleshy stalk called a peduncle. A skin tag is also known as an acrochordon.

As used in the present disclosure, the term "skin surface" refers to the surface of the portion of the skin that is not affected by a skin lesion.

Figure 1B:
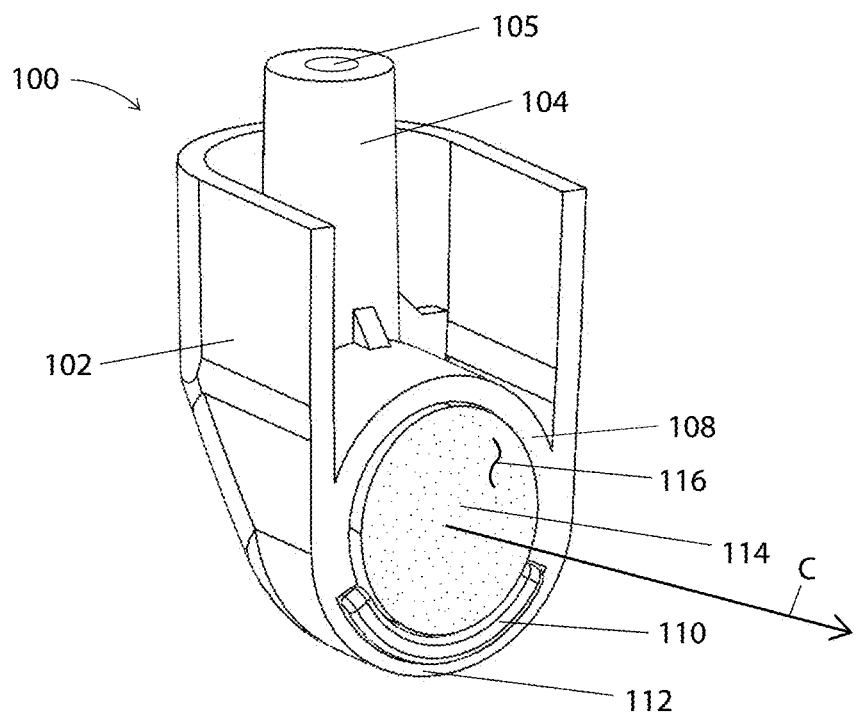

FIGS. 1A and 1B depict a perspective view of an embodiment of tip 100. Tip 100 is depicted in an upright position. Axis A represents a direction parallel to a surface of the skin during typical operation of tip 100, while axis B represents a direction perpendicular to the surface of the skin during the typical operation of tip 100. However, tip 100 is also usable when oriented in different directions, as will be discussed further herein.

The upper part of tip 100 is configured for attachment to a device for supplying cryogenic matter, and the lower part of tip 100 is configured to contact the skin surface of a patient during treatment.

Tip 100 includes a body 102. In exemplary embodiments, the body 102 is made of plastic, and is produced through processes such as die casting, injection molding, or additive manufacturing. Body 102 includes conduit 104 for receiving cryogenic matter. The cryogenic matter is typically a liquid, and may include any liquid that is commonly used in dermatologic applications. For example, the cryogenic matter may include liquid nitrogen, a mixture of dimethyl ether and propane (DMEP), isobutene, isopentane, propane, or 1,1 difluoroethane. The cryogenic matter may be stored in a pressurized manner as a liquid and converted to a gas as it is released into conduit 104. The cryogenic matter may also be stored as an aerosolized liquid with a propellant, and conveyed to the tip as an aerosol mist.

Conduit 104 may be generally L-shaped, with an inlet 105 and an outlet 106 at about 90 degree angles to each other. Outlet 106 opens into cavity 107. In the illustrated embodiment, cavity 107 is generally cylindrical or ovaloid, and is defined by perimeter 108; however, cavity 107 may take any suitable shape for performing the functions described herein.

As shown in FIG. 1B, absorbent application element 114 is sized and shaped to fit within cavity 107 (shown in FIG. 1A). Absorbent application element 114 may be, for example, a bud made of open cell foam. The absorbent application element 114 may be compressible. When cryogenic matter is released out of outlet 106 and into cavity 107, the absorbent application element 114 absorbs the cryogenic matter and become saturated with the cryogenic matter. The cryogenic matter reaches exposed face 116 of the absorbent application element 114, from which it may contact a raised skin lesion.

Tip 100 further includes a strip of conductive material 109. The conductive material 109 may include, for example, a ceramic or a metal, e.g., a sintered metal. Among metallic materials, the conductive material may include, for example, brass, copper, aluminum, or stainless steel. In a preferred embodiment, the conductive material may include stainless steel.

The conductive material 109 includes a lip 110 that extends at least partially around the perimeter 108 of cavity 107. When the tip 100 is placed adjacent to a skin tag, the lip 110 contacts the base of the skin tag. A layer of insulating material 112 is disposed below a portion of the conductive material 109, in order to prevent the conductive material 109 from coming into contact with healthy skin. The insulating material 112 may include plastic. The insulating material 112 may be formed integral with the rest of perimeter 108. In exemplary embodiments, a thickness of the insulating material 112 may be between about 0.5 and about 1.25 mm. Insulating material 112 may not be disposed below lip 110. Lip 110 may protrude in the direction of vector C beyond insulating material 112. Lip 110 may protrude in the direction of vector C beyond exposed face 116. When cryogenic matter is absorbed into absorbent application element 114, the cryogenic matter comes into contact with the conductive material 109. The conductive material 109 conducts the cooling from the portion of the conductive material 109 within cavity 107 to the lip 110.

As shown in FIG. 1B, cryogenic matter exits the exposed face 116 of absorbent application element 114 in the direction of vector C and comes into contact with a skin tag (not shown) oriented adjacent thereto, thereby freezing the skin tag. Simultaneously, the lip 110 comes into contact with the base of the skin tag, thereby freezing the base of the skin tag. Advantageously, because the lip 110 extends below the lowest extent of the absorbent application element 114, the lip 110 contacts a portion of the base of the skin tag that is closer to its junction with the skin surface. In addition, because the lip 110 is of a material different from that of the absorbent application element 114, the user experiences a tactile sensation of the base of the skin tag being contacted and frozen.

Furthermore, the lip 110 is not only located at the very bottom of the perimeter 108, but also extends circumferentially partially outward in either direction from the bottom. As a result, the lip 110 may pinch upon the base of the skin tag regardless of the angle at which the tip 100 is placed upon the skin tag. This functionality is especially advantageous for skin tags located on parts of the body that afford the user difficult sight lines or that may be anatomical locations that are challenging to reach.

Figure 2A:
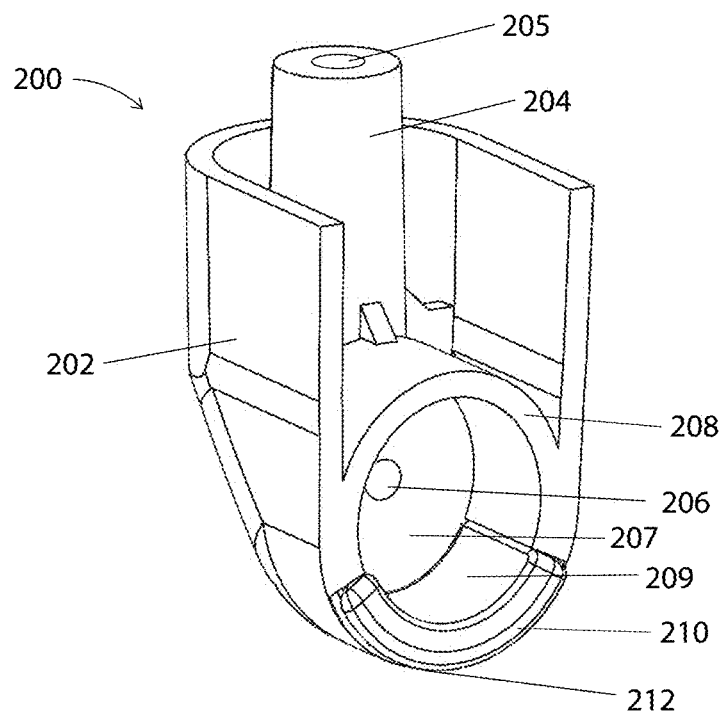
FIGS. 2A and 2B depict another embodiment of a tip for application of cryogenic matter onto a skin lesion, according to embodiments of the present disclosure.
Figure 2B:
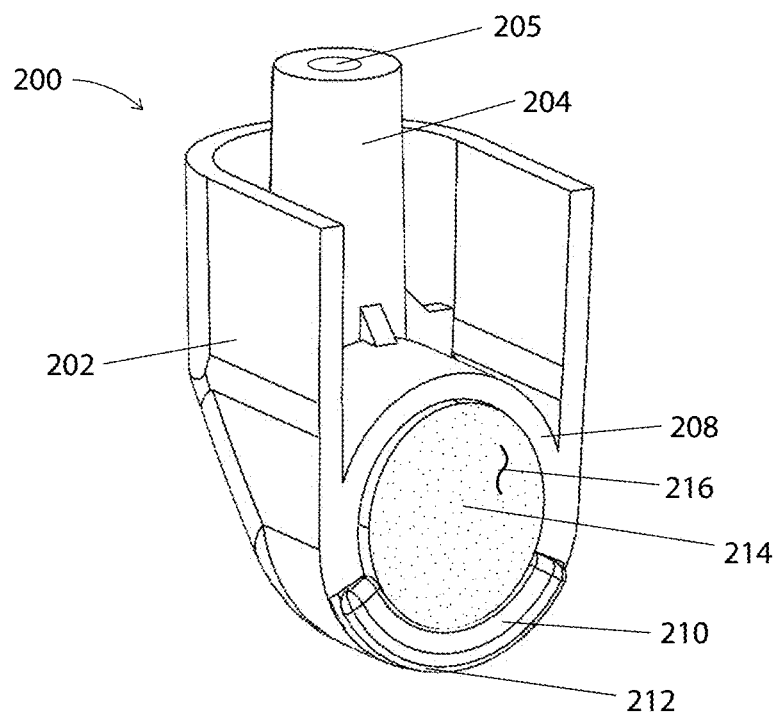

FIGS. 2A and 2B depict an embodiment of a tip 200. Tip 200 may be similar in many respects to tip 100, and accordingly similar reference numerals are used to refer to similar components, except that the reference numerals begin with "2." FIGS. 2A and 2B show body 202, conduit 204, inlet 205, outlet 206, cavity 207, perimeter 208, conductive material 209, lip 210, insulating material 212, absorbent application element 214, and exposed face 216.

A difference between tip 200 and tip 100 is that the lip 210 extends further down on the face of the tip 200 that faces the skin tag (not show), leaving only a very thin space between the bottom of the lip 210 and the skin surface. The distance between the bottom of lip 210 and the skin surface may be approximately 0.5 mm or more or less. Tip 200 is thus particularly well-suited to grasp the base of a skin tag, provided that the user is careful to hold the device containing the tips at an angle perpendicular to the skin, to prevent accidental contacting of the lip 210 with the skin surface.

Figure 3A:
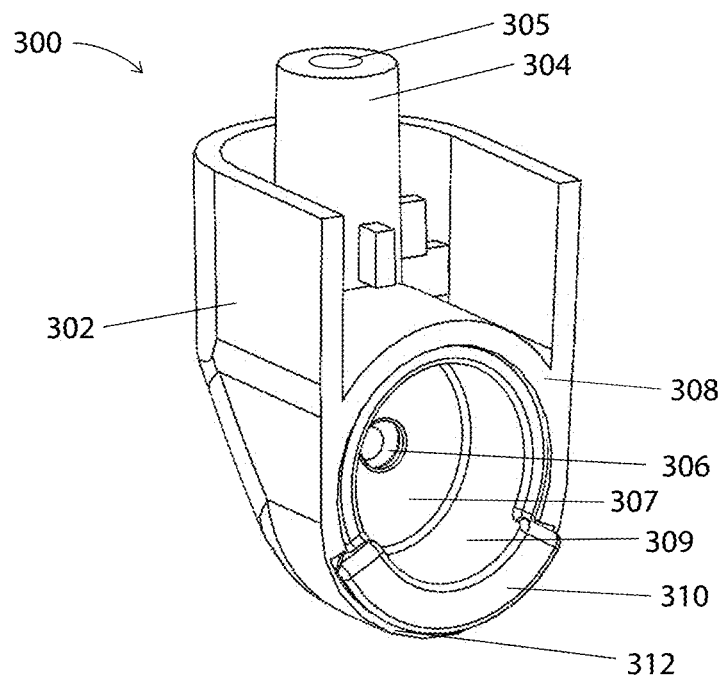
FIGS. 3A and 3B depict another embodiment of a tip for application of cryogenic matter onto a skin lesion, according to embodiments of the present disclosure.
Figure 3B:
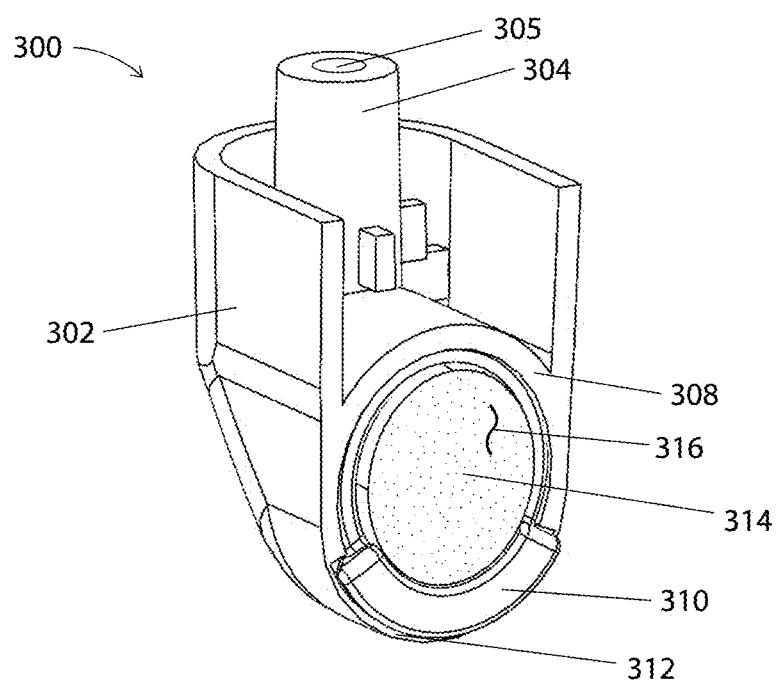

FIGS. 3A and 3B depict an embodiment of a tip 300. Tip 300 may be similar in many respects to tip 100 and tip 200, and accordingly similar reference numerals are used to refer to similar components, except that the reference numerals begin with "3." FIGS. 3A and 3B show body 302, conduit 304, inlet 305, outlet 306, cavity 307, perimeter 308, conductive material 309, lip 310, insulating material 312, absorbent application element 314, and exposed face 316.

A difference between tip 300 and the previous embodiments is that the conductive material 309 includes a casing that extends around an entire interior of the cavity 307, and correspondingly around the external perimeter of the absorbent application element 314. The increase in the amount of conductive material 309 may be advantageous for conducting the cold to the lip 310 quickly and effectively. The lip 310 need not extend around the entire perimeter of the casing, as the casing itself is sufficient to conduct the cold to the lip 310 from multiple directions.

Figure 4A:
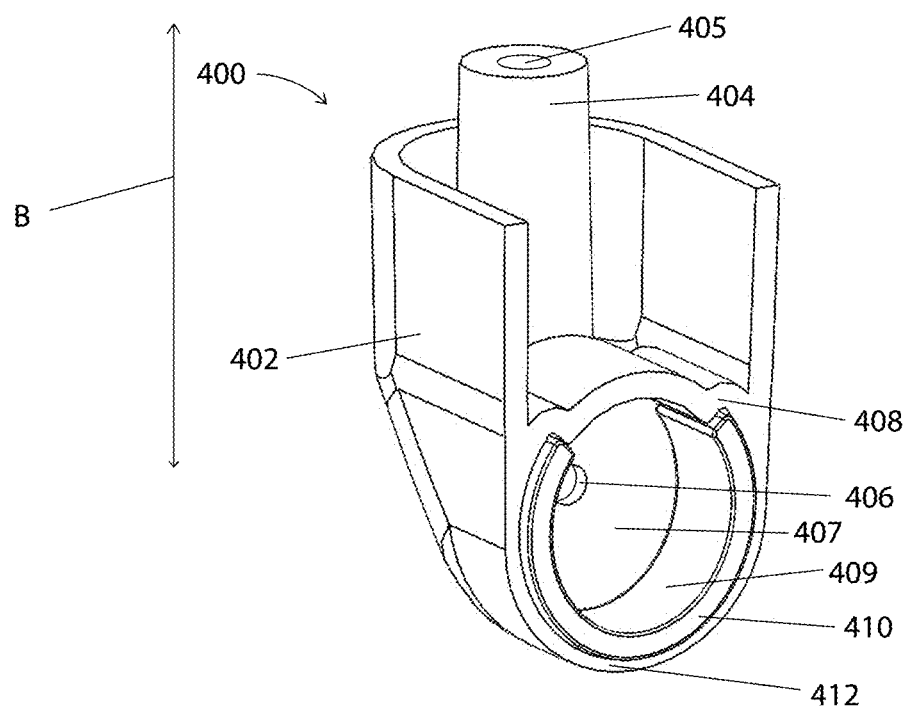
FIGS. 4A and 4B depict another embodiment of a tip for application of cryogenic matter onto a skin lesion, according to embodiments of the present disclosure.
Figure 4B:
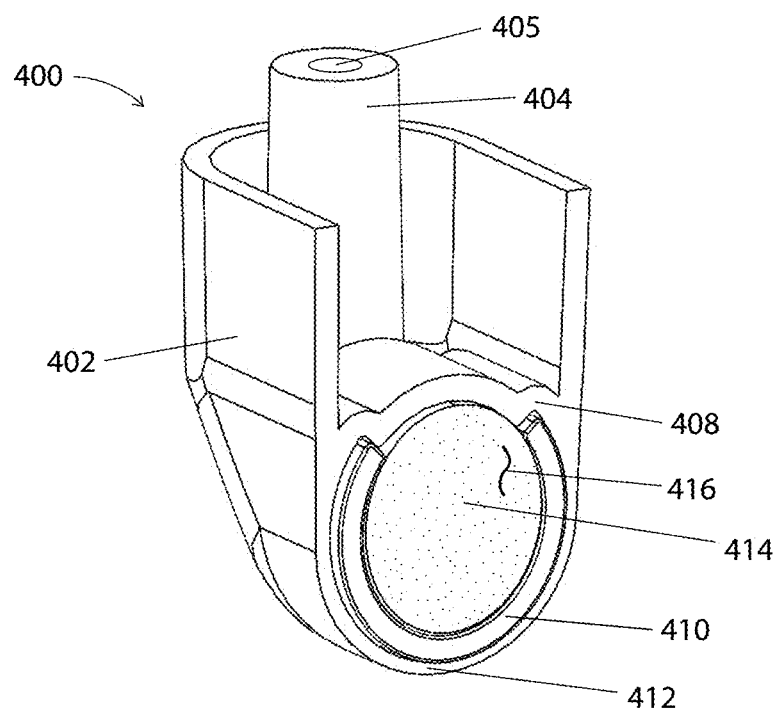

FIGS. 4A and 4B depict an embodiment of a tip 400. Tip 400 may be similar in many respects to tips 100, 200, and 300, and accordingly similar reference numerals are used to refer to similar components, except that the reference numerals begin with "4." FIGS. 4A and 4B show body 402, conduit 404, inlet 405, outlet 406, cavity 407, perimeter 408, conductive material 409, lip 410, insulating material 412, absorbent application element 414, and exposed face 416.

A difference between tip 400 and the previous embodiments of tips is that lip 410, and correspondingly conductive material 409 within cavity 407, extends approximately ¾ of the way around the perimeter 408 of the cavity 407. Advantageously, this configuration of the lip 410 allows the lip to contact the base of the skin tag not only when conduit 404 is parallel to axis B, but also when conduit 404 is deviated from axis B, even up to about 90 degrees.

Figure 5A:
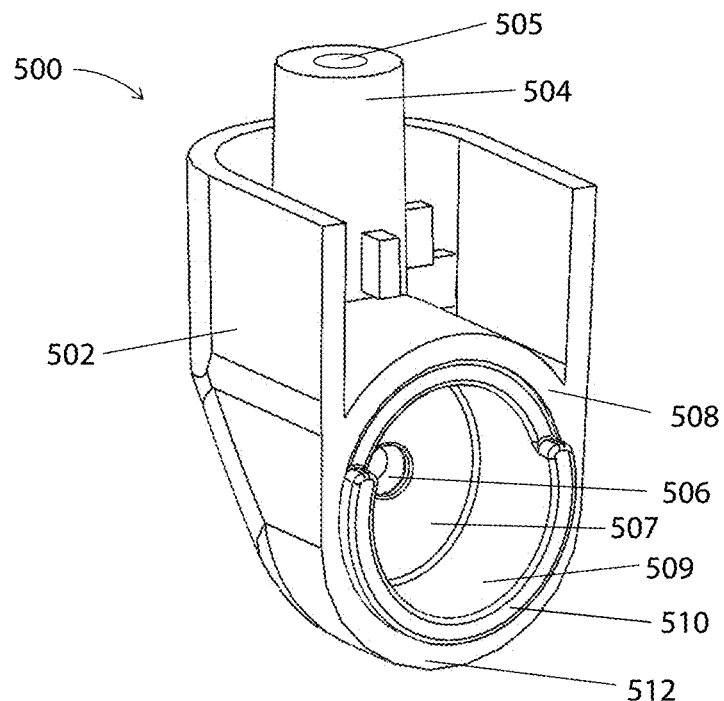
FIGS. 5A and 5B depict another embodiment of a tip for application of cryogenic matter onto a skin lesion, according to embodiments of the present disclosure.
Figure 5B:
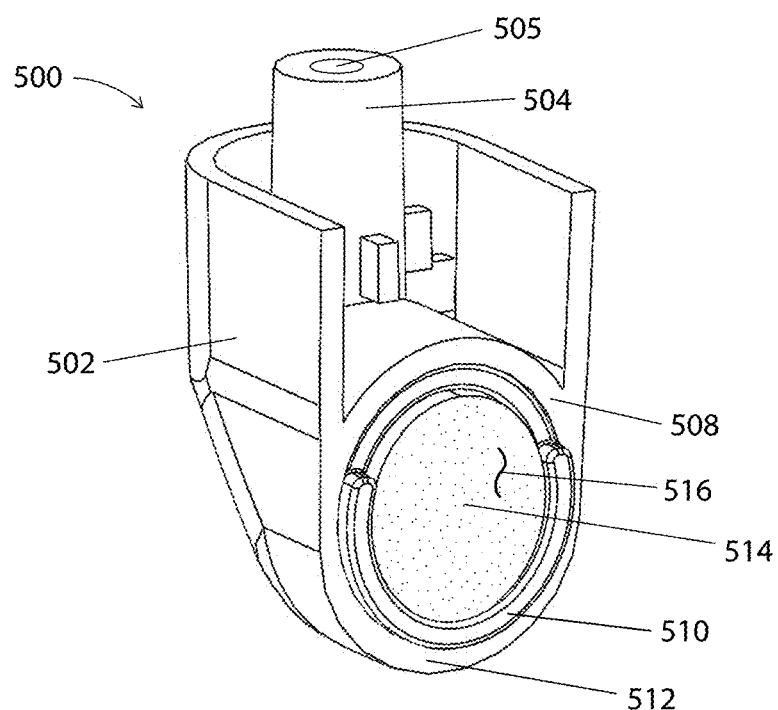

FIGS. 5A and 5B depict an embodiment of a tip 500. Tip 500 may be similar in many respects to tips 100, 200, 300, and 400, and accordingly similar reference numerals are used to refer to similar components, except that the reference numerals begin with "5." FIGS. 5A and 5B show body 502, conduit 504, inlet 505, outlet 506, cavity 507, perimeter 508, conductive material 509, lip 510, insulating material 512, absorbent application element 514, and exposed face 516.

Tip 500 combines the feature of having the conductive material 509 extend along the entire interior of the cavity 507 (analogous to conductive material 309 of tip 300, as shown in FIG. 3A) with the feature of the lip 510 extending approximately ¾ of the way around the perimeter 508 of the cavity 507 (analogous to lip 410 of tip 400, as shown in FIGS. 4A and 4B).

Figure 6:
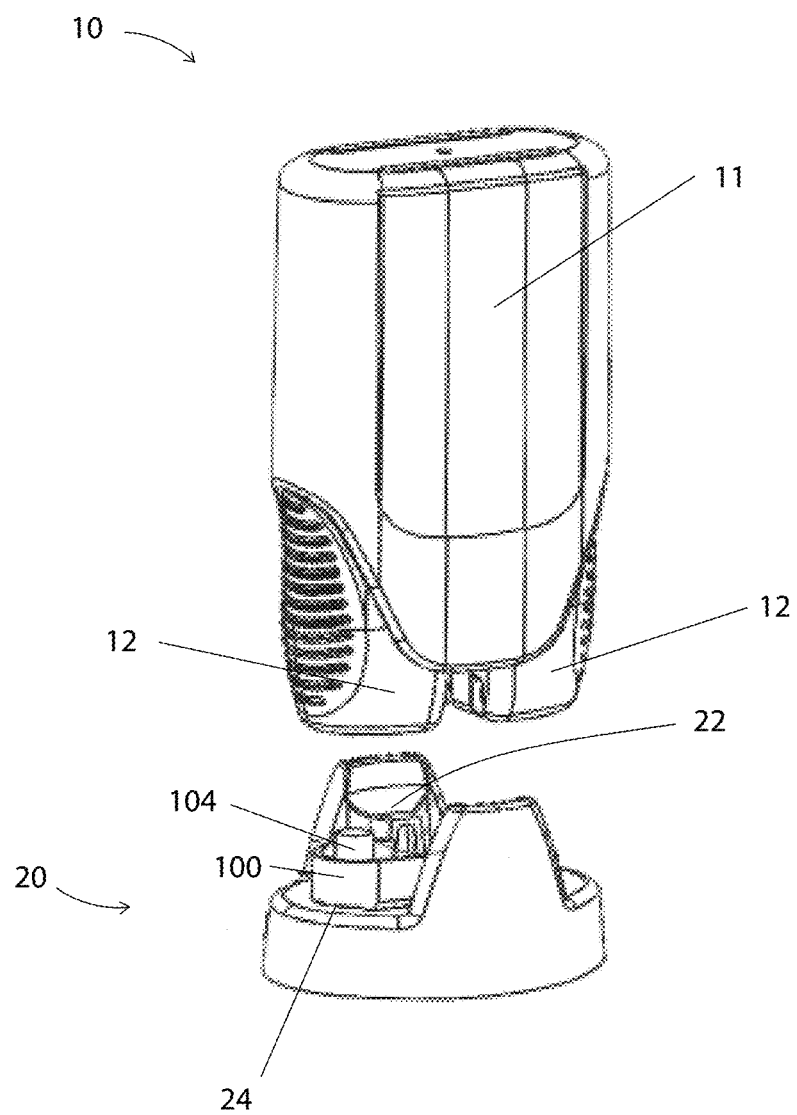
FIG. 6 depicts a tweezers device and charging base for application of cryogenic matter onto a skin lesion, suitable for use with any of the tips of FIG. 1A-5B, according to embodiments of the present disclosure.

Referring now to FIG. 6, tip 100 (or, not shown, any of tip 200, tip 300, tip 400 or tip 500) may be used in combination with a tweezers device 10 and a charging base 20. Tweezers device 10 has an applicator body 11 that includes two arms 12. Each arm 12 includes therein a hollow interior region (not shown). Each hollow interior region includes a canister containing cryogenic matter, and a connector for delivering cryogenic matter from the canister to the conduits of the tips 100. The charging base 20 includes one or more receptacles 24 for holding tips 100, and one or more guiding ridges 22 for receiving therein at least part of applicator body 11 when the arms 12 are connected to the tips 100.

FIGS. 7A-7F illustrate procedural stages of, and device parts involved in, methods for applying cryogenic matter from tweezers device 10 to a skin tag (not shown) via tips 100, using charging base 20 to prime the tips 100. Although FIGS. 7A-7F are described in relation to tips 100, the same description applies equally to tips 200, 300, 400 and 500.

Figure 7A:
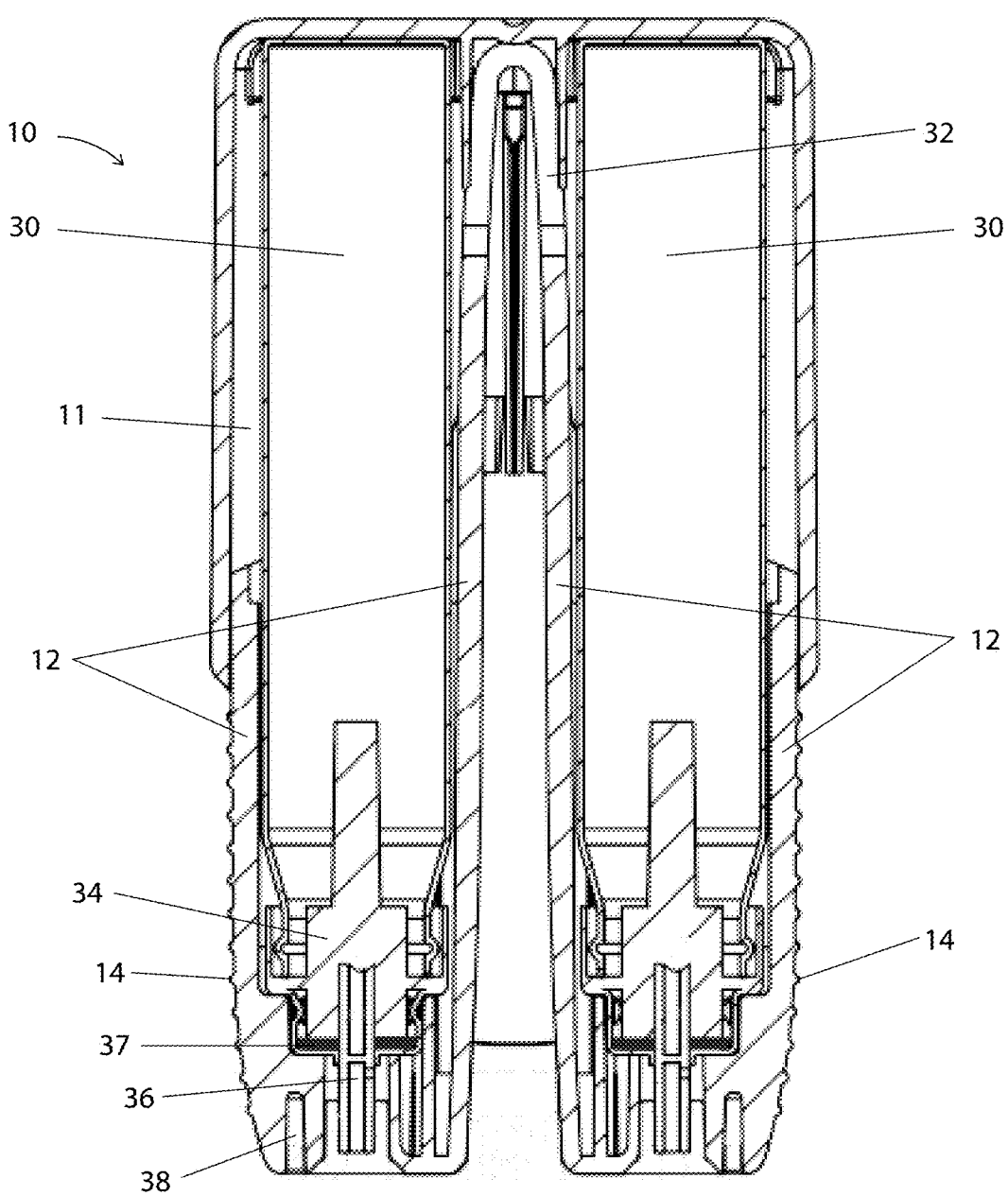
FIGS. 7A-7F depict stages of a method of use of the tweezers device of FIG. 6, according to embodiments of the present disclosure.
Figure 7B:
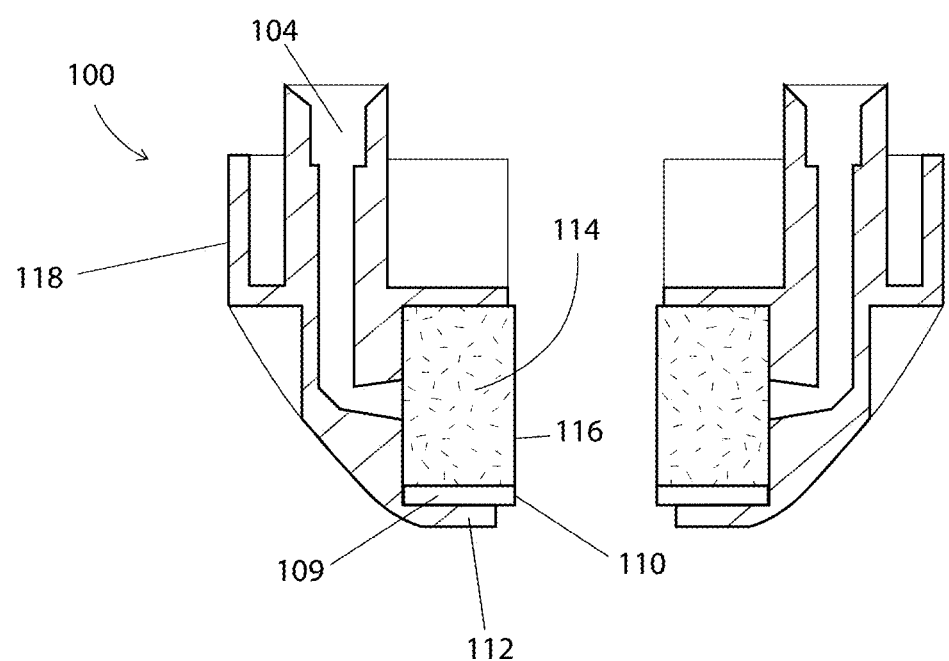

FIG. 7A illustrates a cross-section of a tweezers device 10, and FIG. 7B illustrates a cross-section of a pair of tips 100. The tweezers device 10 may be used with tips 100 that are disposable, and that may be removed and replaced as desired.

Referring to FIG. 7A and FIG. 7B, tweezers device 10 includes an applicator body 11 having two opposed arms or limbs 12. The limbs 12 may be manufactured in one piece via injection molding. Limbs 12 are connected by an integrally molded flexible member 32. The flexible member 32 biases the limbs 12 apart from each other. Tweezers device 10 further includes, on each limb 12, a hand grip 14. Tweezers device 10 is sized to fit within a single hand, so that the user may grasp one hand grip 14 with a thumb, and a second hand grip 14 with the other fingers of the same hand, and thereby squeeze the limbs 12 together.

Each limb 12 includes a canister 30 charged with cryogenic matter. The cryogenic matter is initially stored at high pressure.

Each limb 12 further includes a valve 34 and a conduit 36. Valve 34 may include a spring (not shown). The spring may be formed integrally within the valve. Valve 34, when opened through compression of the spring, permits flow of cryogenic matter from the canister 30 to the conduit 36. For example, the compression of the spring may permit an outlet from the canister 30 to pass through an elastomeric seal 37, placing conduit 36 in fluid communication with the canister 30. The conduit 36 is sized and shaped to form a fluid connection with the conduit 104 of disposable tip 100. The cryogenic matter may flow as a liquid, an aerosol mist, or a gas, as discussed above.

Each limb 12 further includes a depression 38. The depression 38 is sized to match and receive a corresponding arm 118 of tip 100. Placement of depression 38 over arm 118 stabilizes the connection between the tweezers device 10 and tip 100.

Figure 7C:
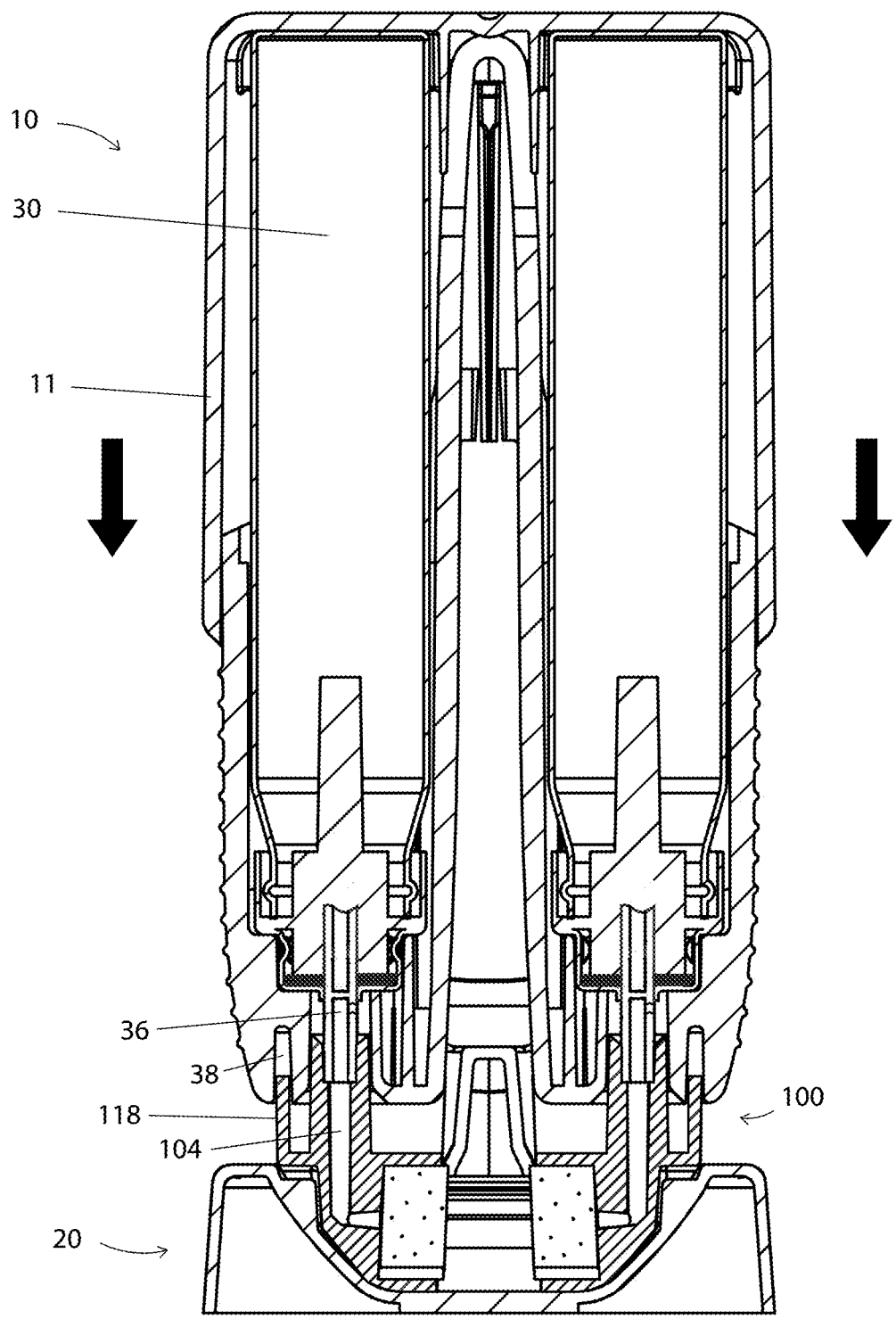

Referring now to FIG. 7C, two tips 100 are placed in opposed positions within charging base 20. The charging base 20 is molded with receptacles 24 (shown in FIG. 6) that are sized to receive therein the tips 100. The user grasps the tweezers device 10 and orients the tweezers device 10 over the charging base 20.

The user then lowers the tweezers device 10 onto the tips 100 (as indicated by the bold downward facing arrows shown on either side of tweezers device 10). Each depression 38 receives therein the corresponding arm 118, and each conduit 36 receives therein the corresponding conduit 104. The tweezers device 10 is thus attached to the tips 100, and is fully supported by the tips 100 disposed within the charging base 20. In an alternative embodiment, instead of placing the tips 100 into the charging base 20, the user may manually attach each of the tips 100 individually to the tweezers device 10, and then place the tweezers device 10 and tips 100 all together into the charging base 20.

Figure 7D:
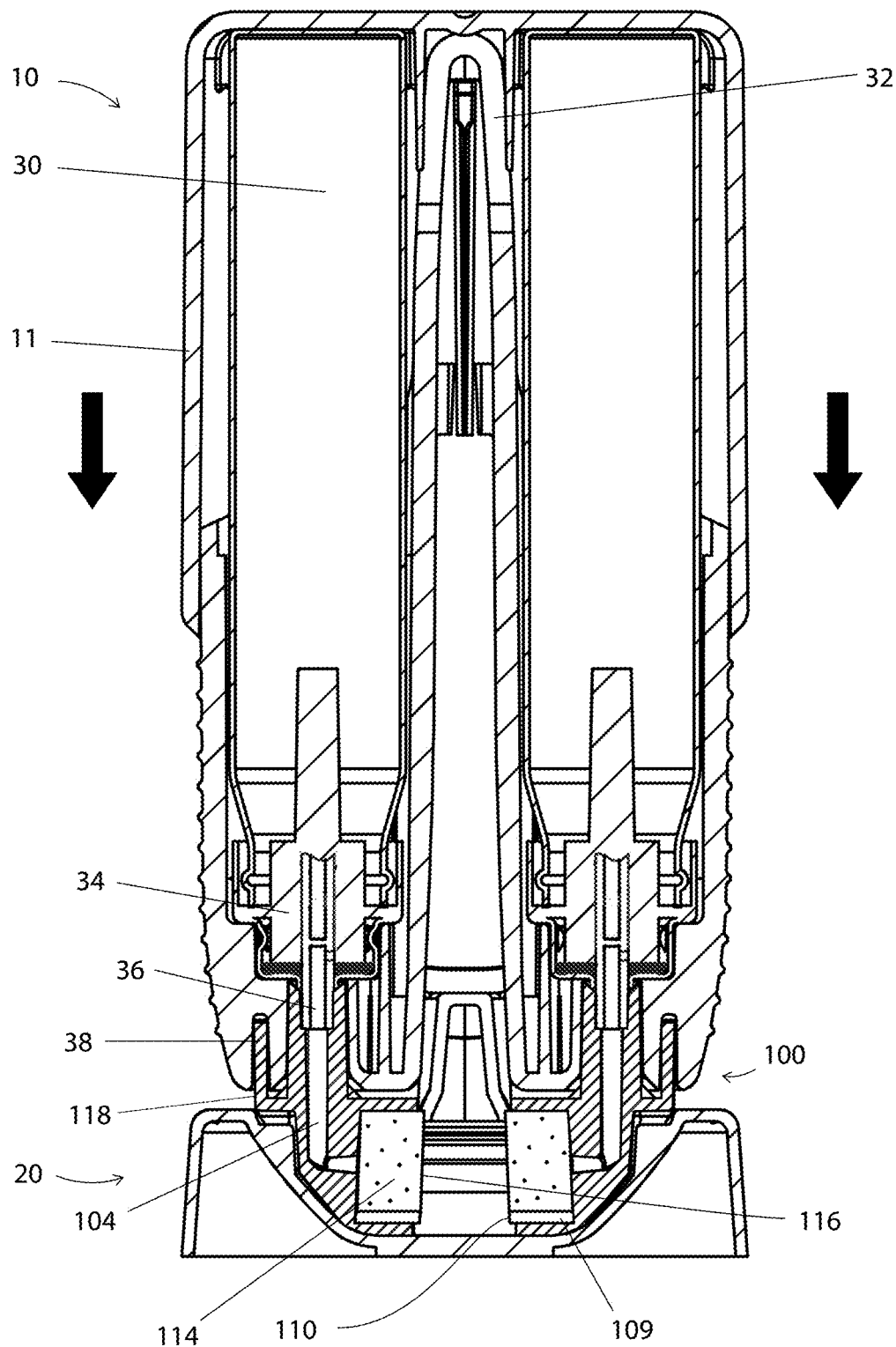

Referring to FIG. 7D, the user further lowers the tweezers device 10 and tips 100 downward within the charging base 20 (as indicated by the bold downward facing arrows shown on either side of tweezers device 10). The arm 118 and conduit 104 of each tip 100 exert an upward pressure on the valve 34, causing compression of the spring therein. Pressurized cryogenic matter is thus permitted to flow from the canister 30 to conduit 36 and to conduit 104. Due to the pressure within each canister 30, the flow of cryogenic matter is unidirectional, out of each canister 30. The valve may be configured to release a bolus of cryogenic matter upon opening of the valve. Alternatively, the valve may permit a continuous stream of cryogenic matter to enter conduit 36 when the valve is open.

From conduit 104, the cryogenic matter enters absorbent application element 114. The cryogenic matter passes through the absorbent application element 114 to exposed face 116. The evaporation of cryogenic matter from within the application element 114 creates a temperature drop within the application element 114. This temperature drop is convected to the adjacent conductive material 109 and conducted to lip 110.

Figure 7E:
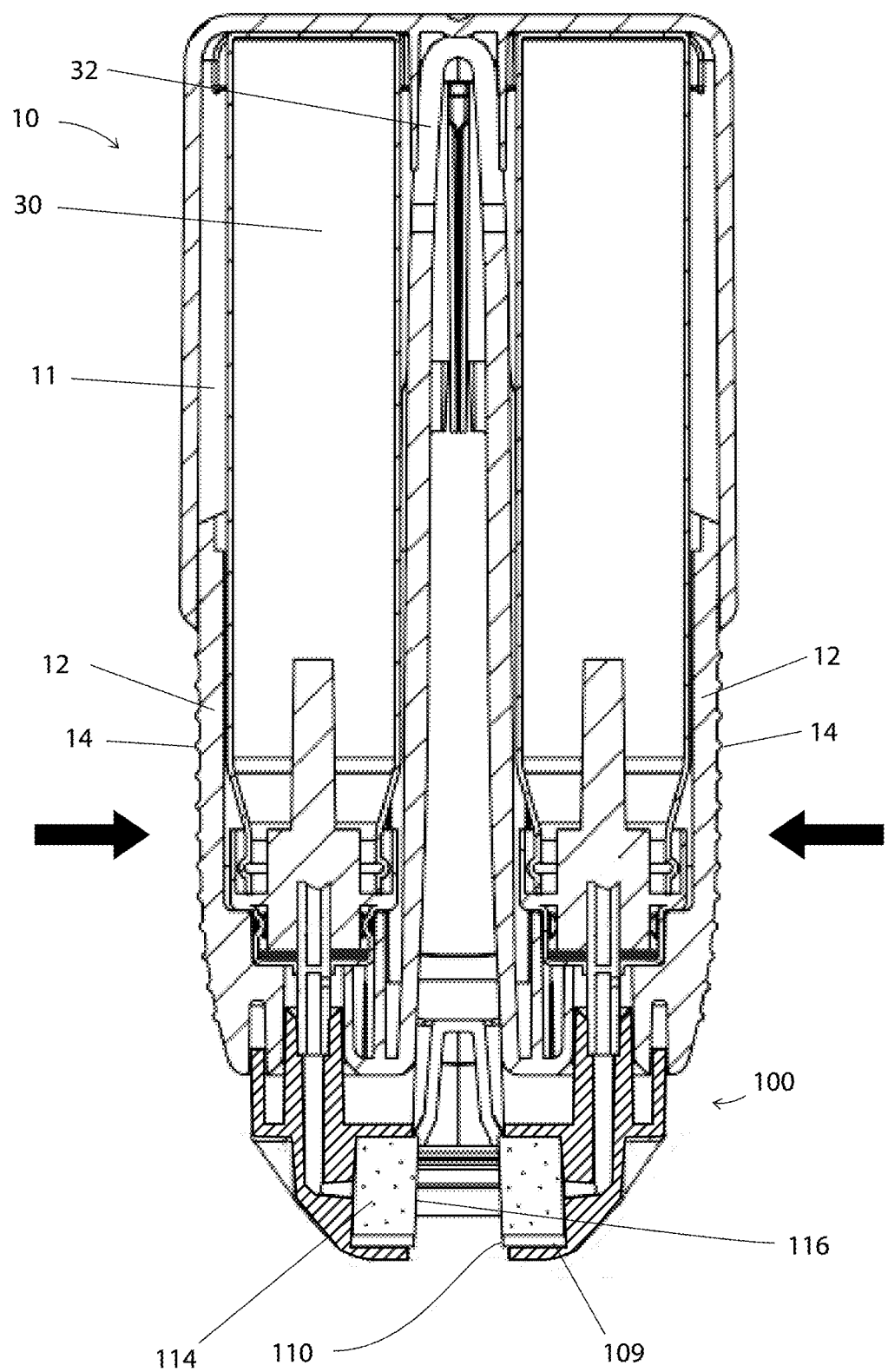

Referring now to FIG. 7E, the user then removes tweezers device 10 from the charging base 20 (shown in FIG. 7D), with the absorbent application element 114 and the thermally conductive material 109 already cooled. The exposed surface 116 and the lip 110 of each tip 100 typically appear visibly frosted. Due to the bias of flexible member 32, the tips 100 are spaced apart, aligned to span opposite sides of the skin tag (not shown). The user grasps the hand grips 14, positions the device 10 adjacent the skin tag, with a tip 100 on either side of the skin tag, and squeezes the limbs 12 inward against the bias of the flexible member 32 (as indicated by the bold inward facing arrows shown on either side of tweezers device 10).

Figure 7F:
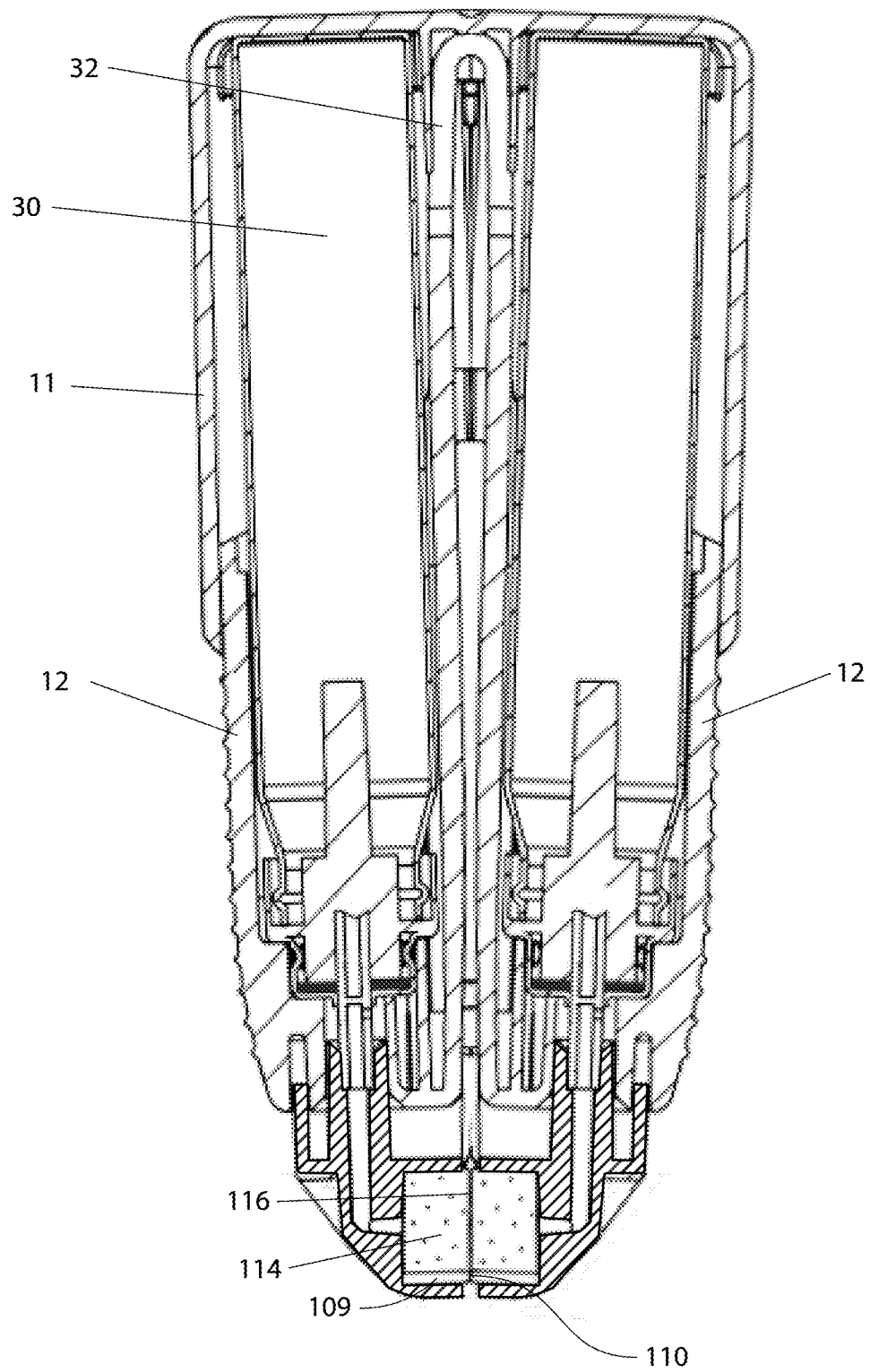

Referring now to FIG. 7F, as a result of squeezing of the limbs 12, the skin tag (not shown) is squeezed in between the cryogenically cooled exposed faces 116 of the (generally compliant) absorbent application element 114 and between the (generally rigid) cryogenically cooled lips 110 of the conductive material 109. The lips 110 and exposed faces 116 completely encapsulate the skin tag. Furthermore, because the (generally rigid) lips 110 jut out from the tips 100 more prominently than the (generally compliant) exposed faces 116, the opposed edges of the lips 110 squeeze and freeze the base of the skin tag even more strongly than do the exposed faces 116 freeze the distal portion of the skin tag. Because of the positioning of the lip 110 around a substantial portion of the perimeter 108 of the tips, the edges of the lips 110 may pinch upon the base of the skin tag over a broad range of values of the angle at which the tip 100 is placed upon the skin tag. The temperature of the tissue of the skin tag is substantially reduced, causing significant irreversible tissue damage, so that the skin tag typically falls off of the skin within several days after treatment.

In the procedure described above, the charging base 20 is positioned below the tweezers device 10 (as shown in FIGS. 7C and 7D), typically on a flat surface. This orientation is often simplest for implementation. It may be possible, however, to actuate the springs (within the spring-actuated nozzle) through any compression of the tweezers device 10 relative to the tips 100, regardless of the orientation of the tweezers device 10 (e.g., even sideways or upside down), and regardless of the specific shape and configuration of the charging base 20. Other actuation mechanisms may likewise be implemented, in a manner known to those of skill in the art.

Figure 8A:
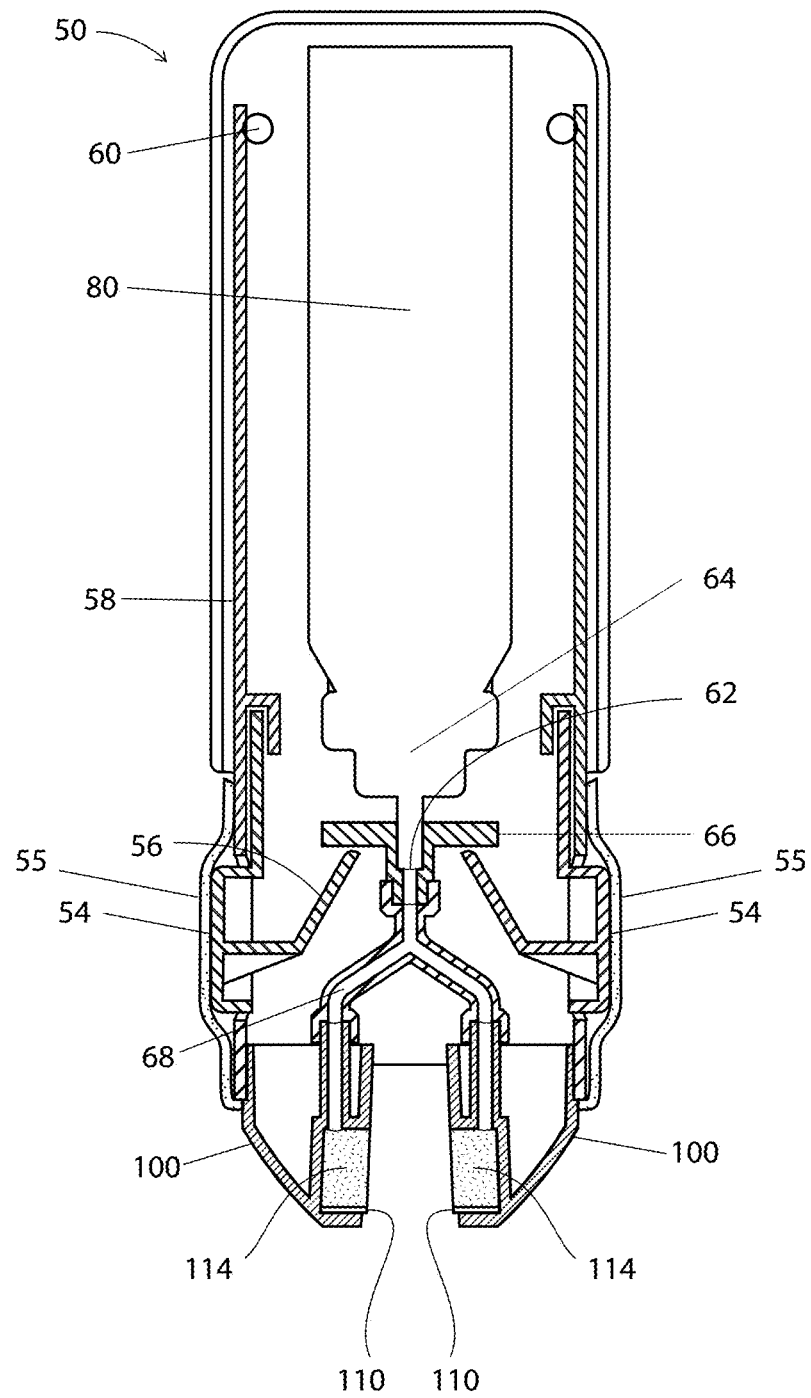
FIGS. 8A-8C depict a tweezers device with a single canister of cryogenic material and an actuation system for charging the tips, suitable for use with any of the tips of FIGS. 1A-5B, according to embodiments of the present disclosure.
Figure 8B:
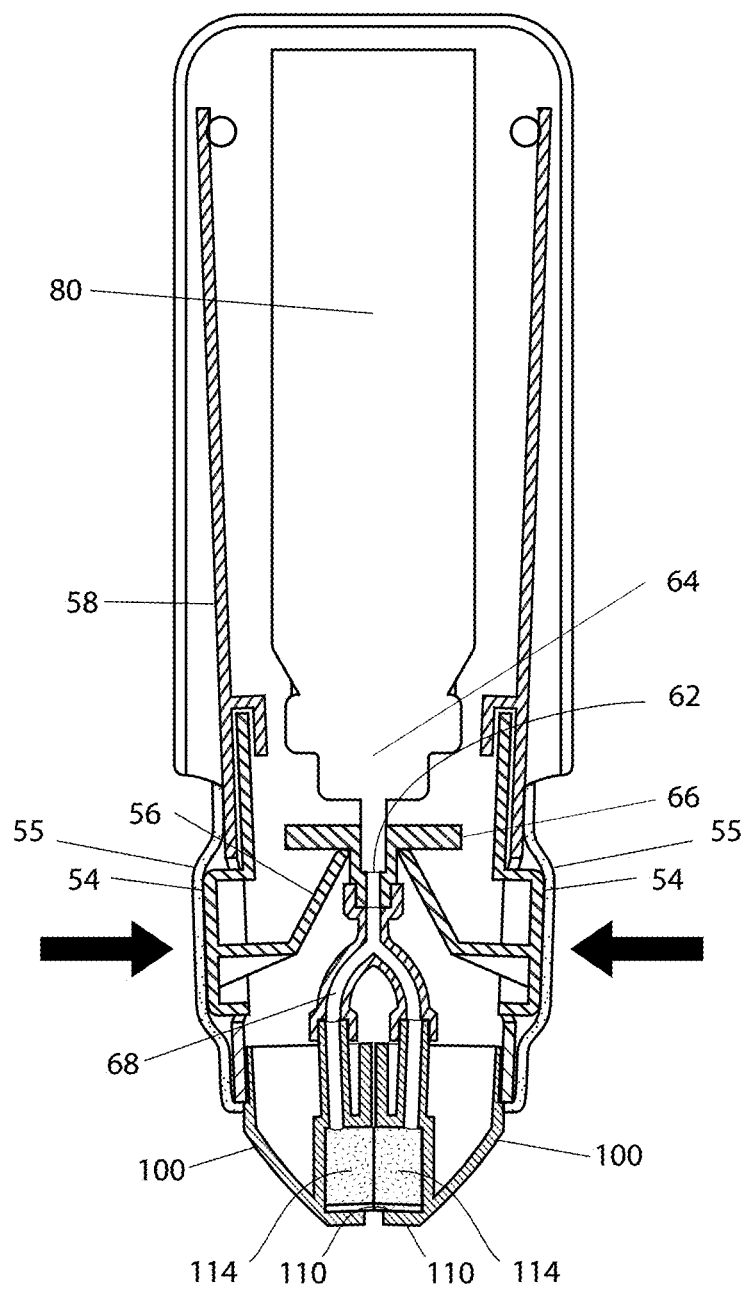
Figure 8C:
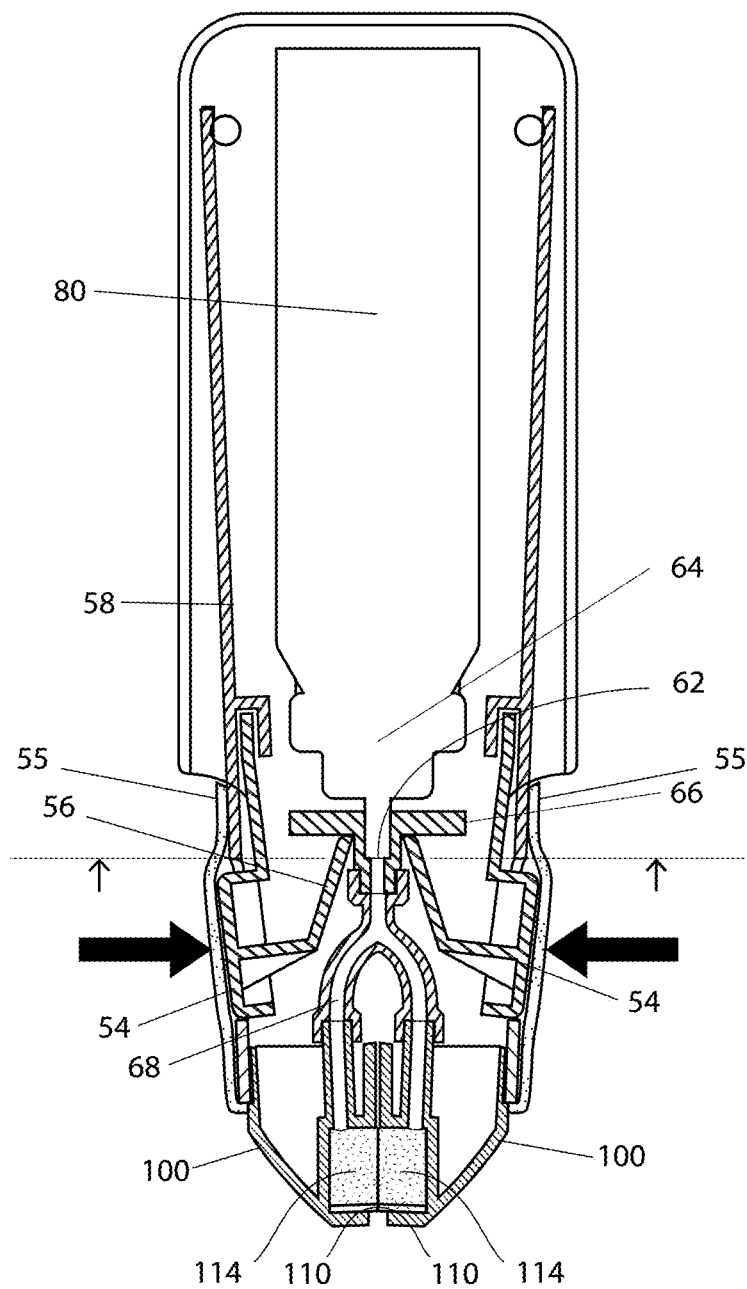

In the previously illustrated embodiments, the cryogenic matter is contained in two separate canisters, which are simultaneously opened by depression of the tips. The cryogenic matter may be contained within a single canister. One exemplary implementation of a tweezers device 50 with such a single canister configuration is illustrated in FIGS. 8A-8C. Tweezers device 50 includes a single canister 80, which stores pressurized cryogenic matter. Canister 80 includes an outlet 62. Outlet 62 is closed by a valve 64 within canister 80, which is configured to be opened through upward movement of member 66. When the valve 64 is open, cryogenic matter is delivered into Y-shaped feeder 68, and thence into tips 100.

Tweezers device 50 further includes hand grips 54, which are operatively connected to internal levers 56. The hand grips 54 are biased outward through the operation of spring or pivot 60 on lever extension 58. Each hand grip 54 may be overlaid with overlayer 55, of an elastomer or other suitable material, providing the user tactile acuity/comfort and thermal insulation.

In operation, as shown in FIG. 8B, the user squeezes hand grips 54 toward each other (as indicated by the bold inward facing arrows shown on either side of tweezers device 50), thereby applying upward force on member 66 via levers 56. As a result, as shown in FIG. 8C, member 66 is raised relative to outlet 62 (as indicated by the upward facing arrows shown on either side of tweezers device 50, with their arrowheads touching a line indicating the plane of an opening of outlet 62). The upward movement of member 66 opens valve 64, and cryogenic matter may flow through Y-shaped feeder 68. Due to the pressure within canister 80, the flow of cryogenic matter is unidirectional, out of canister 80 through Y-shaped feeder 68, and onto and into absorbent application elements 114 and, via elements 114, to lips 110. The flow of cryogenic material may be conducted onto application elements 114 via generally L-shaped conduits with outlets (not shown) disposed out of the plane of view of FIGS. 8A-8C. The flow of cryogenic material may be conducted onto application elements 114 via tip-conduits with respective outlets (not shown) disposed out of the plane of view of FIGS. 8A-8C. The flow of cryogenic material may be conducted onto application elements 114 via tip-conduits with respective outlets disposed in the plane of view of FIGS. 8A-8C.

Other configurations for charging a device with a single canister may also be utilized. For example, the Y-shaped feeder may be sufficiently rigid such that simultaneous application of upward pressure on the tips causes the Y-shaped feeder itself to apply pressure on the canister outlet, thereby opening the valve, similar to the manner described in connection with FIGS. 7A-7F.

Figure 9A:
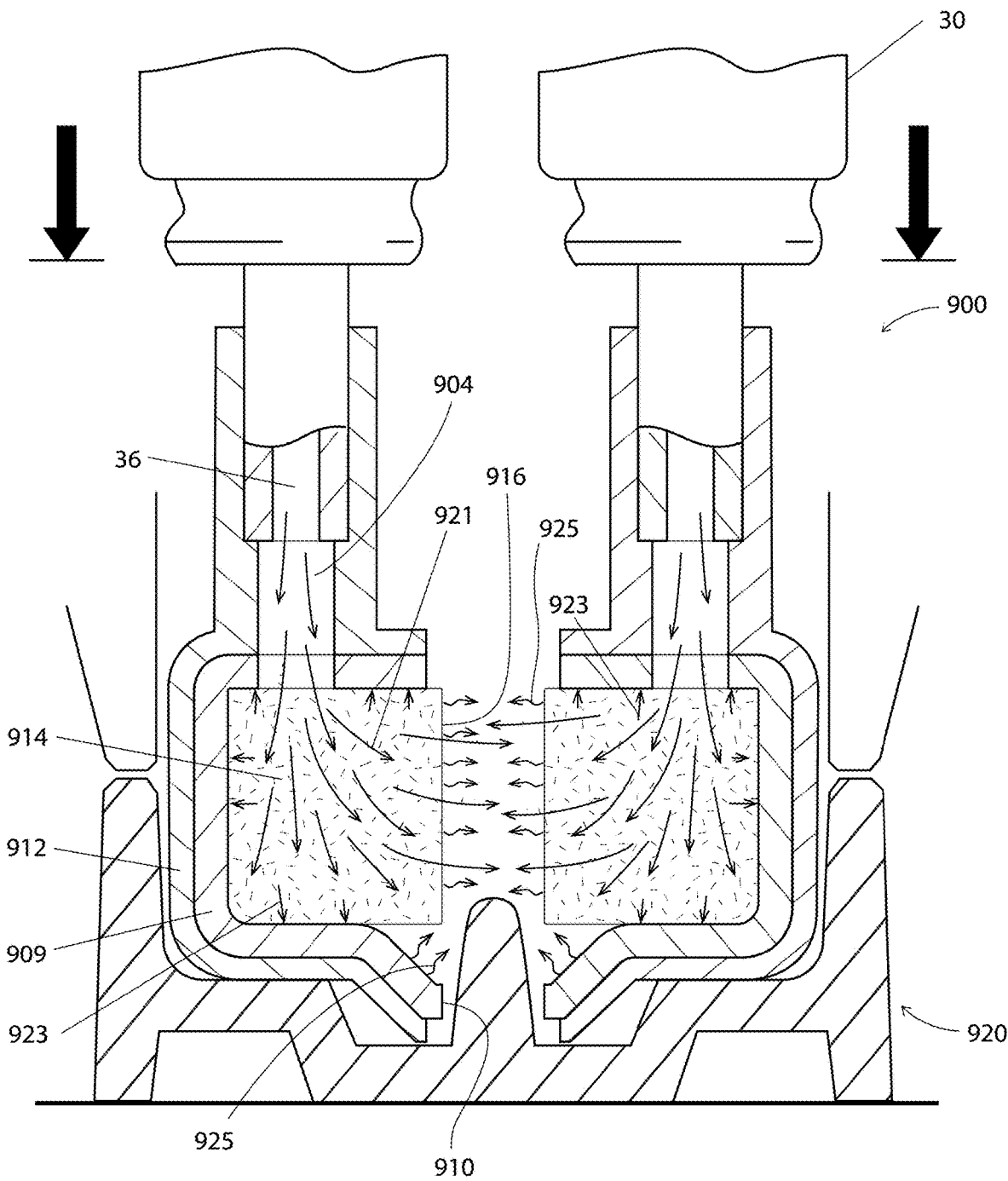
FIGS. 9A-9C depict a tweezers device and stages of use of the tweezers device with another embodiment of a tip for application of cryogenic matter, according to embodiments of the present disclosure.
Figure 9B:
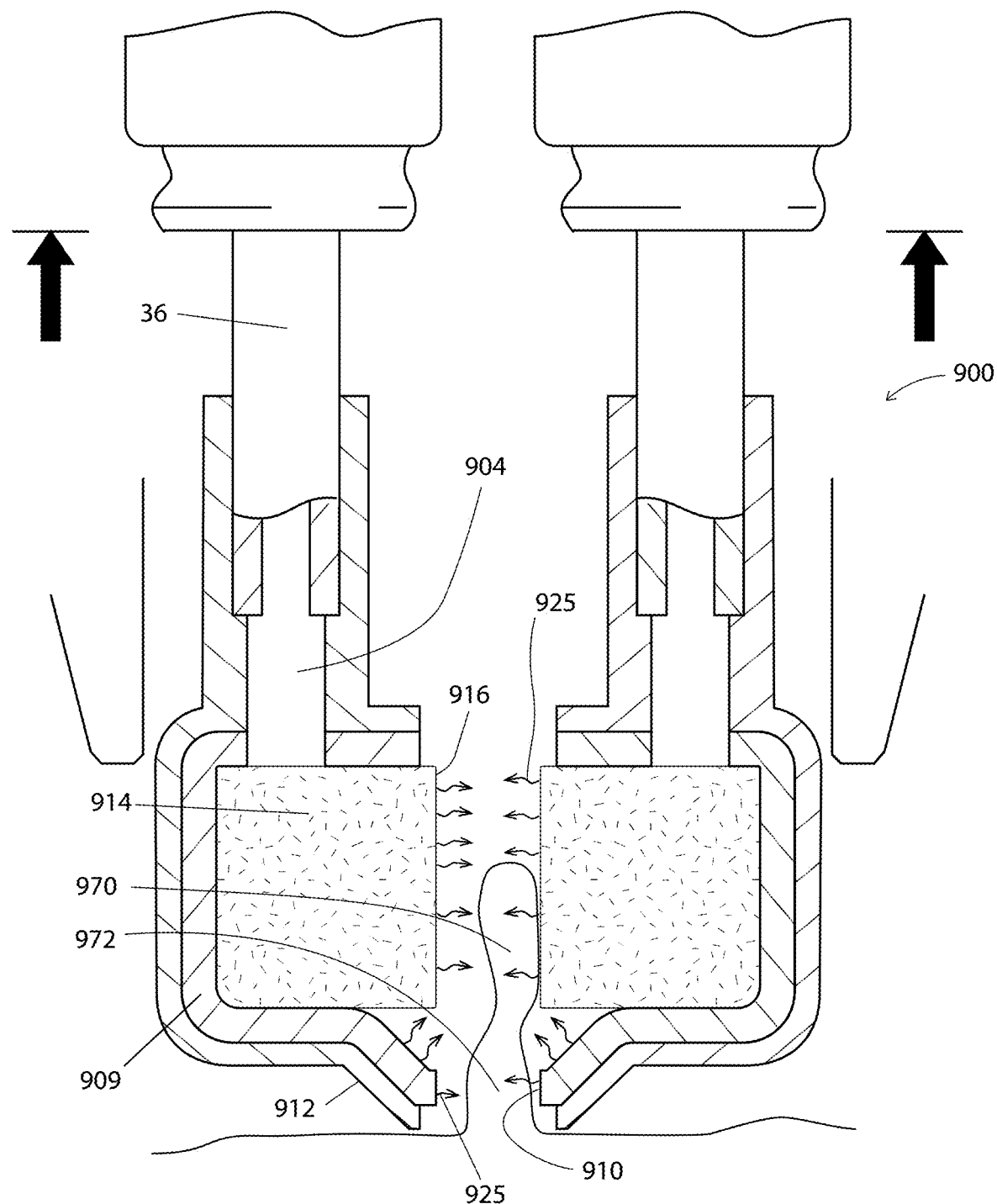
Figure 9C:
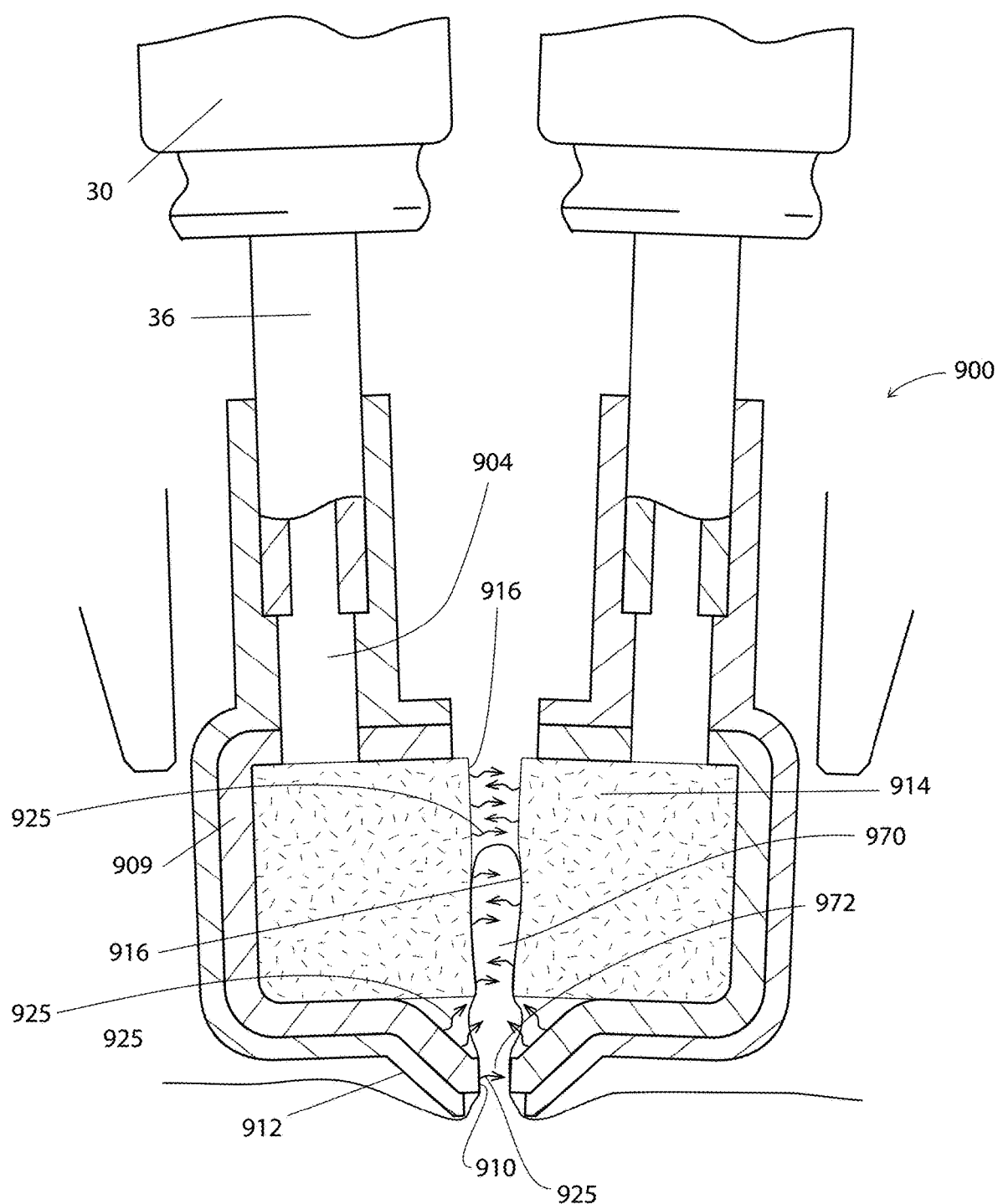

FIGS. 9A-9C depict an embodiment of a tip 900. Tip 900 may be similar in many respects to tips 100, 200, 300, 400 and 500, and accordingly similar reference numerals are used to refer to similar elements, except that the reference numerals begin with "9". FIGS. 9A-9C show conduit 904, conductive material 909, lip 910, insulating material 912, absorbent application element 914, and exposed face 916. FIGS. 9A-9C also show canisters 30 and conduits 36 of FIGS. 7A-7F. FIG. 9A shows charging base 920, similar to charging base 20 of FIGS. 7C and 7D. FIG. 9A shows bold downward facing arrows indicating the user charging tips 900 by pressing conduits 36 down toward charging base 920. FIG. 9B shows bold upward facing arrows indicating the removal of the downward pressing depicted in FIG. 9A. FIGS. 9B and 9C show an illustrative skin tag 970.

A difference between tip 900 and the previous embodiments of tips is that tip 900 has an angled lip 910. The angled lip 910 extends partially below the bottom surface of absorbent application element 914. As shown in FIG. 9A, when the cryogenic matter passes through conduit 36 and into absorbent application element 914 (such passage represented by long arrows 921), cold is convected onto the conductive material 909 (such convection represented by short arrows 923). Furthermore, cold is consequently convected from surfaces 916 of absorbent application elements 914 and from lips 910 to the surrounding air (such convection represented by arrows 925).

FIG. 9B shows the tweezers device placed around skin tag 970, and FIG. 9C shows the tweezers device being squeezed around skin tag 970. The angled lips 910 contact and convect cold and cold air toward/onto base 972 of the skin tag 970, while the exposed surfaces 916 come into contact with and convect cold and cold air toward/onto the distal portion of the skin tag 970.

Figure 10A:
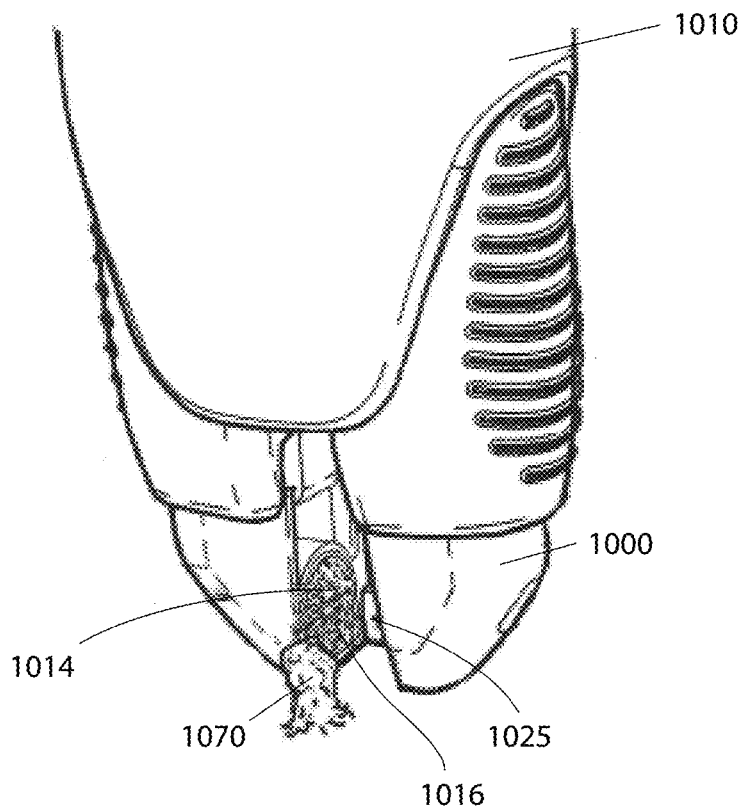
FIGS. 10A and 10B depict a tweezers device including yet another embodiment of a tip for application of cryogenic matter, according to embodiments of the present disclosure.
Figure 10B:
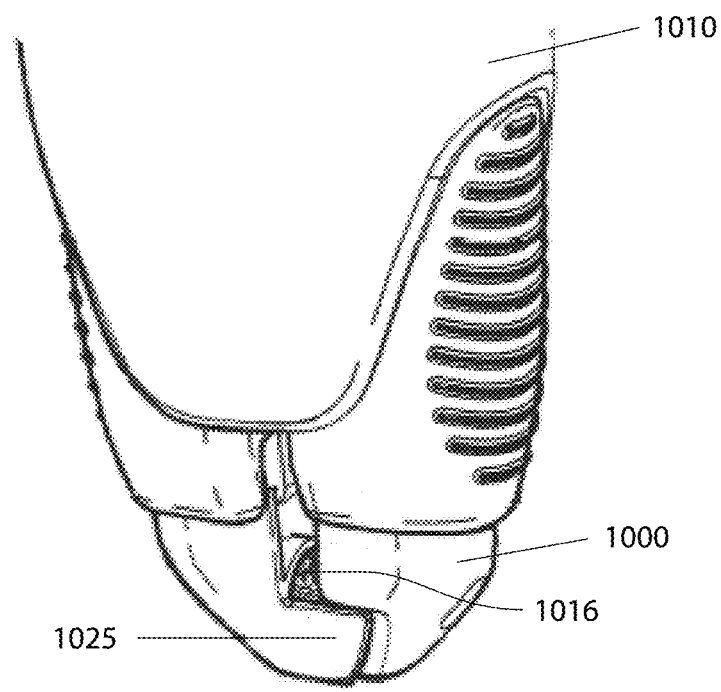

FIGS. 10A and 10B depict an embodiment of a tip 1000. Tip 1000 may be similar in many respects to tips 100, 200, 300, 400, 500 and 900. FIGS. 10A and 10B show absorbent application element 1014 and its exposed face 1016. Each tip 1000 includes a cross spar 1025 on at least one side. In the illustrated embodiment, the tip 1000 is open-ended on one side and includes the cross spar 1025 on the other side. Alternatively, cross spars 1025 may be present on both sides of a tip 1000. FIGS. 10A and 10B also show tweezers device 1010, to which tips 1000 are attached. When the tweezers device 1010 is squeezed, the cross spars 1025 from each tip 1000 extend over the side of the opposing tip 1000. The cross spars 1025 thus prevent the skin tag 1070 from exiting any gap between the tips 1000. The cross spars 1025 may provide further assurance that the tweezers device 1010 will properly squeeze the skin tag. Cross spars 1025 may be implemented in conjunction with any of the embodiments of tips previously described.

Figure 11A:
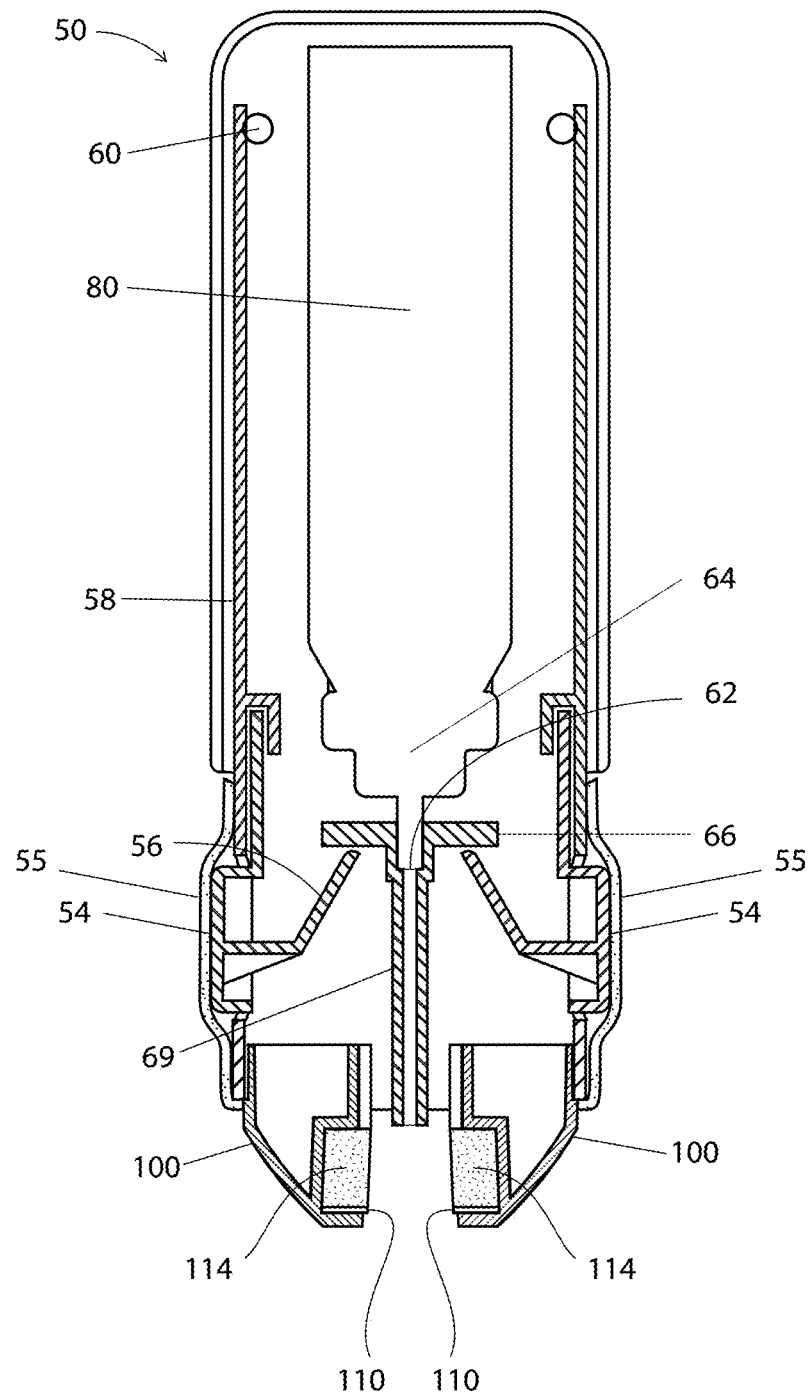
FIGS. 11A-11C depict a tweezers device with a single canister of cryogenic material and an actuation system for charging the tips, according to embodiments of the present disclosure.
Figure 11B:
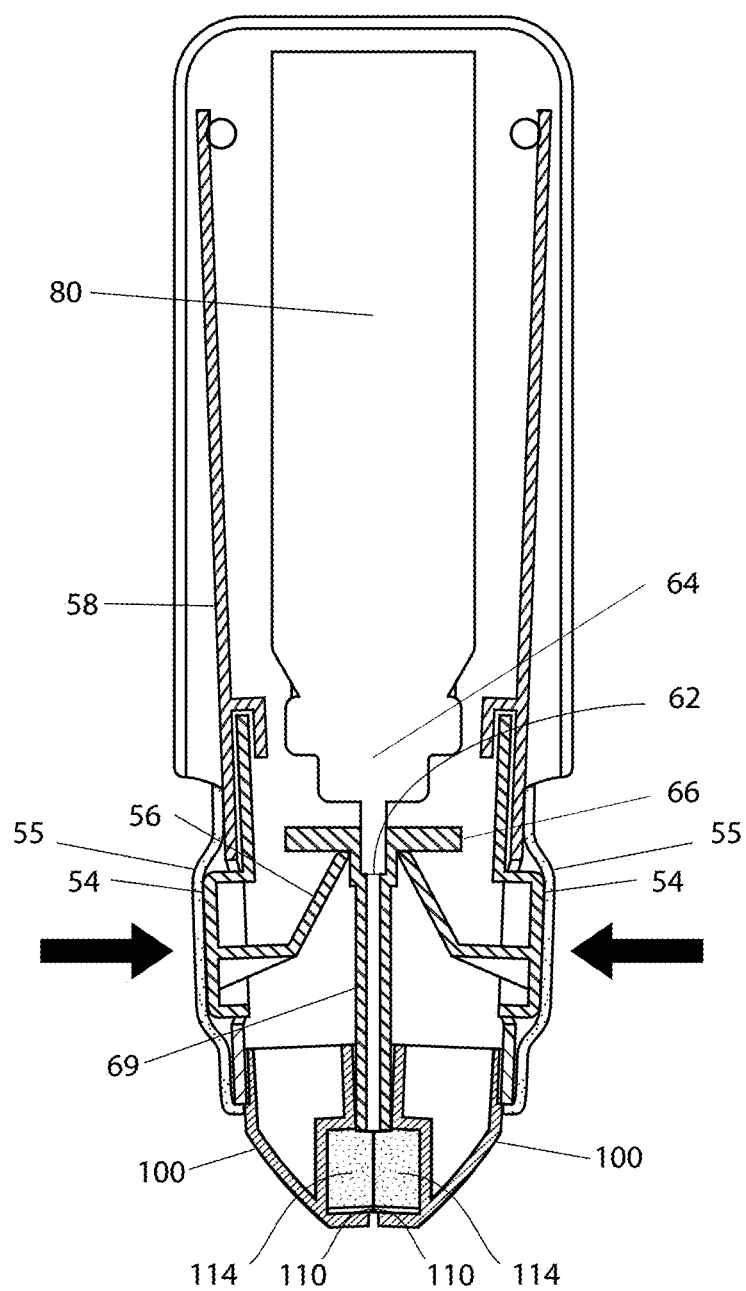
Figure 11C:
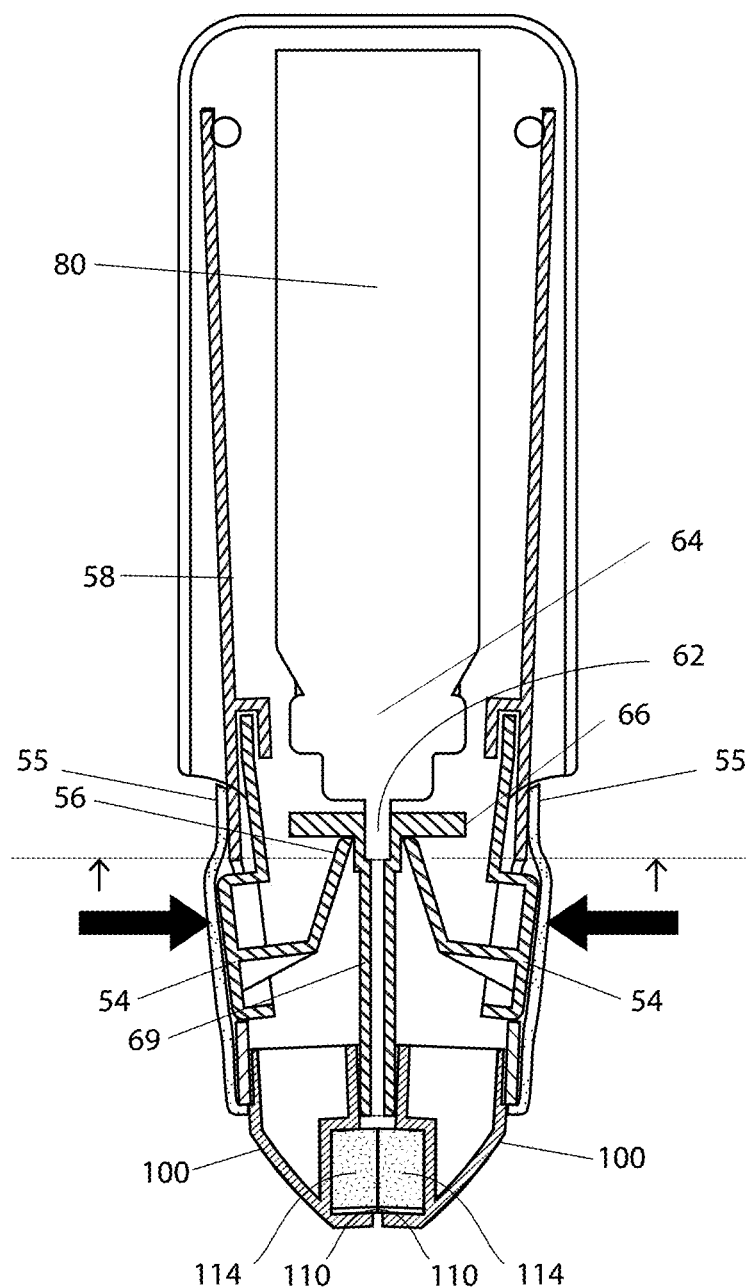

Another exemplary implementation of a tweezers device 50 with a single canister configuration is illustrated in FIGS. 11A-11C. Many of the features shown in the embodiment of FIGS. 11A-11C may be similar or identical to those shown in FIGS. 8A-8C. Features in FIGS. 11A-11C identical in configuration and/or function to those in FIGS. 8A-C are numbered the same as in in FIGS. 8A-C. For instance, in FIGS. 11A-11C, tweezers device 50 includes a single canister 80, which stores pressurized cryogenic matter. Canister 80 includes an outlet 62. Outlet 62 is closed by a valve 64 within canister 80, which is configured to be opened through upward movement of member 66.

When valve 64 is open, cryogenic matter is delivered, not into Y-shaped feeder 68 shown in FIGS. 8A-C, but rather into straight-tube feeder 69, and thence to tips 100. Each of tips 100 may include a region concavely contoured to accept a convex section of the straight-tube feeder that at least partly surrounds an outlet of the straight-tube feeder.

In operation, as shown in FIG. 11B, the user squeezes hand grips 54 toward each other (as indicated by the bold inward facing arrows shown on either side of tweezers device 50), thereby applying upward force on member 66 via levers 56. As a result, as shown in FIG. 11C, member 66 is raised relative to outlet 62 (as indicated by the upward facing arrows shown on either side of tweezers device 50, with their arrowheads touching a line indicating the plane of an opening of outlet 62). The upward movement of member 66 opens valve 64, and cryogenic matter may flow through straight-tube feeder 69. Due to the pressure within canister 80, the flow of cryogenic matter is unidirectional, out of canister 80 through straight-tube feeder 69, and directly onto and into absorbent application elements 114 and, via elements 114, to lips 110.

Absorbent application elements 114 are compressed against each other during delivery and, in operation, also compressed about a skin tag (not shown) by the user squeezing the handgrips 54 toward each other, as indicated in FIG. 11C by the bold inward facing arrows shown on either side of tweezers device 50. Cold convected from the surfaces of absorbent application elements 114 compressed about a distal portion of the skin tag freezes that portion, and cold convected from lips 110 freezes a base of the skin tag.

Other configurations for charging a device with a single canister may also be utilized. For example, the straight-tube feeder may be sufficiently rigid such that simultaneous application of upward pressure on the tips causes the straight-tube feeder itself to apply pressure on the canister outlet, thereby opening the valve, similar to the manner described in connection with FIGS. 7A-7F.

Thus, apparatus and methods for use of an improved tip for application of cryogenic matter onto a skin lesion such as a skin tag have been provided. Persons skilled in the art will appreciate that the present invention can be practiced by other than the described embodiments, which are presented for purposes of illustration rather than of limitation. The present invention is limited only by the claims that follow.

What is claimed is:

1. A device for application of cryogenic matter directly on a skin lesion, comprising:
    an applicator body having first and second opposing tweezer arms,
    a canister containing cryogenic matter;
    first and second disposable tips, each disposable tip mechanically connected to an end of a respective tweezer arm; and
    a Y-shaped feeder for delivery of cryogenic matter from an outlet of the canister to the first and second disposable tips;
    wherein each tweezer arm includes an actuation mechanism that, when relaxed, seals the cryogenic matter in the canister, and, when actuated, allows the cryogenic matter to flow from the canister to the Y-shaped feeder,
    wherein each tip includes:
        a conduit configured to receive therein the cryogenic matter;
        a compliant absorbent application element configured to absorb and contain the cryogenic matter and having:
            an exposed face configured to apply the cryogenic matter directly onto the skin lesion when the cryogenic matter is delivered from the canister through the conduit to the application element; and
            a bottom surface configured to be closest to skin collateral to the skin lesion when the device is arranged perpendicular to a skin surface;
        and:
        a thermally conductive material in contact with at least a portion of the absorbent application element, wherein said thermally conductive material:
            is configured to conduct cold from the absorbent application element; and
            includes a rigid lip;
    and
    wherein the rigid lip extends, at a distal end, partially below the bottom surface of the absorbent application element.

2. The device of claim 1, wherein the actuation mechanism includes a valve member positioned between the outlet of the canister and an inlet of the Y-shaped feeder, wherein actuation of the actuation mechanism displaces the valve member, thereby opening a valve, allowing the cryogenic matter to flow from the outlet to the inlet.

3. The device of claim 2, wherein the actuation mechanism further comprises a hand grip on each tweezer arm, each hand grip operatively connected to a lever, in the tweezer arm, configured to displace the valve member.

4. The device of claim 3, wherein the hand grip on the first tweezer arm and the hand grip on the second tweezer arm are configured to be gripped toward each other:
    bringing the respective ends of the two tweezer arms toward each other; and
    squeezing together the respective tips upon the skin lesion.

5. The device of claim 1, wherein:
    when cryogenic matter is delivered from the canister to the application elements of the first and second disposable tips when the first and second opposing tweezer arms are placed on either side of the skin lesion and then squeezed together upon the skin lesion:
        the lips of the first and second disposable tips freeze a base of the skin lesion; and
        the exposed faces of the absorbent application elements of the first and second disposable tips freeze a distal portion of the skin lesion.

6. The device of claim 1, wherein the thermally conductive material comprises a casing disposed around an entire perimeter of the absorbent application element.

7. The device of claim 6, wherein the lip extends around less than an entire perimeter of the casing.

8. The device of claim 1, wherein the thermally conductive material includes stainless steel.

9. The device of claim 1, wherein the absorbent application element comprises open cell foam.

10. The device of claim 1, further comprising a charging base configured to receive at least the disposable tips and to receive at least part of the applicator body, the charging base including:
    a plurality of receptacles configured to hold the disposable tips therein; and
    a plurality of guiding ridges configured to receive at least part of the applicator body during attachment of the applicator body to the disposable tips held within the receptacles.

11. The device of claim 1, wherein each lip is angled downward away from the respective absorbent application element.

12. The device of claim 1, wherein each disposable tip further comprises at least one cross spar, wherein the cross spar of the first disposable tip is configured to close over a side of the second disposable tip when the opposing tweezer arms are closed together upon the skin lesion.

13. A device for application of cryogenic matter directly on a skin lesion, comprising:
    an applicator body having first and second opposing tweezer arms,
    a canister containing cryogenic matter;
    first and second disposable tips, each disposable tip mechanically connected to an end of a respective tweezer arm and including:
        a compliant absorbent application element configured to absorb and contain the cryogenic matter and having:
            an exposed face configured to apply the cryogenic matter directly onto the skin lesion when cryogenic matter is delivered, from the canister, to the application element; and
            a lowest edge configured to be closest to a junction of the absorbent application element with a skin surface;
        and:

a thermally conductive material in contact with at least a portion of the absorbent application element, said thermally conductive material:
configured to conduct cold from the absorbent application element; and
includes a rigid lip;
and:
wherein the rigid lip extends below the lowest edge of the absorbent application element when the tweezer arms are oriented perpendicular to skin surface.

14. The device of claim 13, wherein each tweezer arm includes an actuation mechanism that, when relaxed, seals the cryogenic matter in the canister, and, when actuated, allows the cryogenic matter to flow from an outlet of the canister, the actuation mechanism including:
a valve closing the outlet; and
a displaceable valve member configured to open the valve when the valve member is displaced.

15. The device of claim 14, wherein the actuation mechanism further comprises a hand grip on each tweezer arm, each hand grip operatively connected to a lever, in the tweezer arm, the lever configured to displace the valve member.

16. The device of claim 15, wherein each of the first and second disposable tips comprises a conduit configured to receive the cryogenic material therein, the device further comprising a Y-shaped feeder configured to deliver the cryogenic matter from the outlet of the canister to the respective conduits of the first and second disposable tips when the valve is opened, allowing the cryogenic matter to flow from the canister to the Y-shaped feeder.

17. The device of claim 16, wherein the valve member is positioned between the outlet of the canister and an inlet of the Y-shaped feeder, wherein actuation of the actuation mechanism by gripping together the hand grips displaces the valve member, thereby opening the valve, allowing the cryogenic matter to flow from the outlet to the inlet.

18. The device of claim 15, wherein the hand grip of the first tweezer arm and the hand grip of the second tweezer arm are configured to be gripped toward each other:
bringing the respective ends of the two tweezer arms toward each other;
squeezing together the respective tips upon the skin lesion; and
delivering the cryogenic matter from the canister onto the absorbent application elements.

19. The device of claim 13, wherein the lip is angled downward away from the absorbent application element, wherein downward is defined as a direction toward the skin collateral to the skin lesion when the tweezer arms are arranged perpendicular to the skin.

20. The device of claim 19, wherein the lip extends at least partially downward away from a bottom surface of the absorbent application element, wherein said bottom surface lies:
at least partly perpendicular to the exposed face; and,
when the tweezer arms are arranged perpendicular to the skin collateral the skin lesion, closer to the skin than other surfaces of the absorbent application element lying at least partly perpendicular to the exposed face.

21. The device of claim 20, wherein, when cryogenic matter is delivered from the canister to the application elements of the first and second disposable tips when the first and second opposing tweezer arms are placed on either side of the skin lesion and then squeezed together upon the skin lesion:
the lips of the first and second disposable tips freeze a base of the skin lesion; and
the exposed faces of the absorbent application elements of the first and second disposable tips freeze a portion of the skin lesion further away from the collateral skin than the base of the skin lesion.

22. The device of claim 20, wherein downward extension of the lip away from the bottom surface of the absorbent application element increases in a direction paralleling the bottom surface and, from within the absorbent application element, toward the exposed face.

23. The device of claim 13, wherein the absorbent application element comprises open cell foam.

24. The device of claim 13, wherein each disposable tip further comprises at least one cross spar, wherein the cross spar of the first disposable tip is configured to close over a side of the second disposable tip when the ends of the opposing tweezer arms are closed together upon the skin lesion.

25. The device of claim 13, further comprising a charging base configured to receive at least the disposable tips and to receive at least part of the applicator body, the charging base including:
a plurality of receptacles configured to hold the disposable tips therein; and
a plurality of guiding ridges configured to receive at least part of the applicator body during attachment of the applicator body to the disposable tips held within the receptacles.

* * * * *